United States Patent
Lella et al.

(10) Patent No.: US 12,319,744 B2
(45) Date of Patent: Jun. 3, 2025

(54) TREATMENT AND PREVENTION OF HEMOPHILIC ARTHROPATHY WITH AN ANTIBODY AGAINST ENDOTHELIAL CELL PROTEIN C RECEPTOR (EPCR)

(71) Applicant: BOARD OF REGENTS, THE UNIVERSITY OF TEXAS SYSTEM, Austin, TX (US)

(72) Inventors: Vijaya M. Lella, Tyler, TX (US); Usha R. Pendurthi, Tyler, TX (US); Jhansi L. Magisetty, Tyler, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1003 days.

(21) Appl. No.: 17/273,965

(22) PCT Filed: Sep. 5, 2019

(86) PCT No.: PCT/US2019/049656
§ 371 (c)(1),
(2) Date: Mar. 5, 2021

(87) PCT Pub. No.: WO2020/051277
PCT Pub. Date: Mar. 12, 2020

(65) Prior Publication Data
US 2021/0355231 A1    Nov. 18, 2021

Related U.S. Application Data

(60) Provisional application No. 62/727,613, filed on Sep. 6, 2018.

(51) Int. Cl.
*A61P 19/02* (2006.01)
*A61K 38/48* (2006.01)
*C07K 16/28* (2006.01)
*A61K 39/00* (2006.01)

(52) U.S. Cl.
CPC ...... *C07K 16/2896* (2013.01); *A61K 38/4846* (2013.01); *A61P 19/02* (2018.01); *A61K 2039/54* (2013.01)

(58) Field of Classification Search
CPC . C07K 16/2896; A61P 19/02; A61K 38/4846; A61K 2039/54
See application file for complete search history.

(56) References Cited

U.S. PATENT DOCUMENTS

| | | |
|---|---|---|
| 4,376,110 A | 3/1983 | David et al. |
| 4,704,692 A | 11/1987 | Ladner |
| 4,853,871 A | 8/1989 | Pantoliano et al. |
| 4,946,778 A | 8/1990 | Ladner et al. |
| 5,260,203 A | 11/1993 | Ladner et al. |
| 5,455,030 A | 10/1995 | Ladner et al. |
| 8,153,766 B2 | 4/2012 | Xu et al. |
| 9,127,072 B2 | 9/2015 | Xu et al. |
| 9,657,111 B2 | 5/2017 | Zhao et al. |
| 2003/0199444 A1 | 10/2003 | Knudsen |
| 2012/0164150 A1 | 6/2012 | Xu et al. |
| 2015/0210994 A1 | 7/2015 | Margaritis et al. |
| 2016/0229922 A1 | 8/2016 | Kitazawa et al. |
| 2017/0319532 A1 | 11/2017 | Chen et al. |

OTHER PUBLICATIONS

Keshava et al., Factor VIIa interaction with EPCR modulates the hemostatic effect of rFVIIa in hemophilia therapy: mode of its action; 2017, Blood Advances, 1(15): 1206-1214. (Year: 2017).*
Liaw et al. "Identification of the Protein C/Activated Protein C Binding Sites on the Endothelial Cell Protein C Receptor," The Journal of Biological Chemistry, 2000, vol. 276, No. 11, pp. 8364-8370.
Sen et al. "Factor VIIa Bound to Endothelial Cell Protein C Receptor Activates Protease Activated Receptor-1 and Mediates Cell Signaling and Barrier Protection," Blood, 2011, vol. 117, No. 11, pp. 3199-3208.
Sundaram et al. "Blockade of Endothelial Cell Protein C Receptor Augments Factor VIIa Hemostatic Effect in Hemophilia Treatment," Blood, 2014, vol. 124, No. 19, pp. 3031-3033.
Zintner et al. "Gene-Based FVIIa Prophylaxis Modulates the Spontaneous Bleeding Phenotype of Hemophilia A Rats," Blood Advances, 2019, vol. 3, No. 3, pp. 301-311.
International Search Report and Written Opinion issued in PCT/US2019/049656, dated Nov. 15, 2019, 12 pgs.

* cited by examiner

*Primary Examiner* — Daniel E Kolker
*Assistant Examiner* — James Ryland Melchior
(74) *Attorney, Agent, or Firm* — Rothwell, Figg, Ernst & Manbeck, P.C.

(57) ABSTRACT

An antibody, preferably a blocking antibody, and most preferably a monoclonal antibody (mAb), specific for human endothelial cell protein C receptor (EPCR) such as mAbs JRK 1494 or JRK 1535 is used to reduce or attenuate joint swelling, macrophage infiltration, iron deposition and/or blood vessel formation and to treat arthropathy in a hemophilic subject.

19 Claims, 21 Drawing Sheets

TREATMENT AND PREVENTION OF HEMOPHILIC ARTHROPATHY WITH AN ANTIBODY AGAINST ENDOTHELIAL CELL PROTEIN C RECEPTOR (EPCR)

STATEMENT OF RIGHTS TO INVENTIONS MADE UNDER FEDERALLY SPONSORED RESEARCH

This invention was made with government support (NIH HL107483) awarded by the National Institutes of Health. The government has certain rights in the invention.

BACKGROUND OF THE INVENTION

Field of the Invention

The invention in the field of biochemistry, immunology, and medicine relates to the inhibition of hemophilic arthropathy using an antibody or antibodies specific for the endothelial protein C receptor (EPCR).

Description of the Background Art

Hemophilia A occurs in 1 in 5,000 male live births, and Hemophilia B occurs in 1 in 20,000 male live births in the U.S. The number of hemophilia patients in the U.S. has been estimated to be 20,000 (and >400,000 worldwide). Annual treatment costs in the US per patient have been estimated at $100,000 to $500,000 (with extreme cases costing $21 million/year). Total annual medical costs to treat hemophilia in the US has been estimated to be $4.6 billion ($230,000 per patient). Global annual medical cost for hemophilia care is believed to be at least $12 billion. Hemophilia treatment with clotting factors has been categorized as on demand or prophylactic; gene therapy is currently in clinical trials. A number of recombinant FVIII and FIX therapeutic agents have recently approved or in late-phase clinical development (S W Pipe, *Hematology Am Soc Hematol Educ Prog.* 2016; 2016 (1):650-656

The long term goals of prophylaxis have been:

Prevention of sequelae of chronic disease

Prevention of pain and suffering

Improvement in quality of life for the patient and his family

Reduction in long-term societal costs through prevention of disability, improved outcome and maximization of human potential (See, for example, K. Fischer et al., *Haemophilia*, 2003, 9(4):376-81 and *Haemophilia*, 2003, 9 Suppl 1:75-81.

Recently devised therapies for patients with hemophilia and hemophilia who are given inhibitors in clinical trials include the following:

| Category | Agent | Mechanism of Action | Administration | $T_{1/2}$* |
|---|---|---|---|---|
| Targeting the on switch | Emicizumab (ACE910) | Bispecific Ab binds FIXa and FX mimicking FVIIIa to generate thrombin | SC injection (weeks vs monthly dosing) | 30 d |
| Targeting the off switch | Fitusiran (ALN-AT3) | Antithrombin knockdown via si RNA | SC injection | 7 d |
| | Concizumab (Mab20121) | TFPI inhibitor | SC or IV injection | 7 d |
| | APC-specific serpin | APC inhibitor | SC or IV injection | 5-7 d |
| Other Agents | rFVIIa-FP (CSL689) | Extended half-life rFVIIa-albumin fusion protein | IV | 6-10 h |
| | Obizur (OBI-1, BAX901) | B-domain deleted porcine FVIII; reduced cross-reactivity with FVIII inhibitors | IV | 10-12 h |

*half life

In addition to the above, there are or have been a number of other clinical trials by various pharmaceutical companies with different variations of the above.

Hemophilic arthropathy is a debilitating joint disease that develops as a consequence of frequent bleeding in joints in hemophilia patients. Hemophilic arthropathy leads to joint deformities, cartilage, and bone destruction. See, e.g., FIG. 9. Prophylactic treatment of hemophilia patients with clotting factor replacement reduces joint bleeding and hemophilic arthropathy.

All currently approved treatments for hemophilia are based on administration of procoagulant clotting factors, which are labile, short-lived, and expensive to produce. The present invention, as described herein provides a solution and improvement to the disadvantages and deficiencies of some of these current approaches. The present invention relies on the use of an antibody to the EPCR. EPCR is a member of the Class I MHC family of receptors. EPCR is constitutively expressed in endothelium, acts as the receptor for anti-coagulant protein C. EPCR promotes the activation of protein C, and the activated protein C (APC) inactivates clotting factors Factor Va (FVa) and Factor VIIIa (FVIIIa) by cleaving them. EPCR is also expressed on many other cell types. The present inventors' group and others have established that Factor VIIa (FVIIa. the clotting factor that initiates the activation of the coagulation cascade upon binding to tissue factor (TF) binds to EPCR. See FIGS. 1 and 2A-C. See also: Ghosh S et al., *J Biol Chem* 2007; 282: 11849-57; Preston R J et al., *J Biol Chem* 2006; 281:28850-7; Lopez-Sagaseta J et al. *J Thromb Haemost* 2007; 5:1817-

24). FVIIa binding to EPCR on the endothelium or in cells expressing TF induces cell signaling by activating protease activated receptor-1 (PAR1) either directly or by enhancing TF-FVIIa-FXa cleavage of PAR1 (See FIG. 2C) (Sen P et al., *Blood* 2011; 117:3199-208; Disse, J et al., *J Biol Chem* 2011; 286:5756-67).

Centelles, M N et al. ("Blocking EPCR accelerates thrombus development in vivo", *Thromb Haemost.* 2010 June; 103:1239-44) discloses production of monoclonal antibodies (mAbs) against murine EPCR and the testing of their ability to block protein C/activated protein C (APC) binding. The ferric chloride carotid artery injury model in mice was chosen to test the effect of anti-EPCR mAb on thrombus formation. The time to total occlusion of the vessel was analyzed in three groups, given an isotype control mAb (IC), a blocking anti-EPCR mAb (RCR-16) and a non-blocking anti-EPCR mAb (RCR-20). mAb RCR-16 prevented the interaction between protein C/APC and EPCR as demonstrated by surface plasmon resonance and flow cytometry, and inhibited the activation of protein C on the endothelium. Control IC and RCR-20 were unable to induce such effects. In vivo, RCR-16 shortened the time to total vessel occlusion compared with IC [13.4±1.0 (mean±SD) and 17.8±3.2 minutes, respectively, p<0.001]. Occlusive thrombi lasting for more than one hour were observed in all RCR-16-treated animals, but only in 43% of IC-treated ones. Results with RCR-20 were indistinguishable from those with IC. Thus, the document alleges a direct relationship between blocking EPCR and thrombosis. The paper notes that blocking anti-EPCR autoantibodies can predispose to thrombosis episodes and may constitute a new therapeutic target. It should be noted that all proteins involved in the prevention of bleeding also play a role in thrombosis as the processes are essentially the same. In animal studies, thrombosis is always provoked rather than being a natural process. A number of proteins and antibodies, such as FVIIa and modified APC that promote thrombosis have been approved or are on the market for treating hemophilia patients.

U.S. 2016/90229922 (Kitazawa et al.) discloses a pharmaceutical composition for the treatment of a hemorrhagic disease such as hemophilia, acquired hemophilia, von Willebrand disease caused by functional abnormality or deficiency in vWF, and acquired von Willebrand disease (para 0026, sec. 2). The document discloses that principal sites of bleeding in hemophilia include in joints which progresses to joint disorder or "hemophilic arthropathy". This is said to be one of the primary factors in reducing the quality of life in hemophiliacs. The document notes the same disadvantages of clotting factor therapy vs. advantages of antibody therapy as is noted by the present inventors. Kitazawa et al. composition comprises an agent that inhibits the activation of protein C (to APC) or the activity of APC, typically an anti-protein C antibody. Such an antibody is clearly different from an anti-EPCR antibodies of the present invention; Kitazawa et al. teaches the concept that inhibiting protein C activation with an antibody is useful for treating hemophilic arthropathy.

U.S. Pat Publ. 2009/0110683, U.S. Pat. Nos. 8,153,766, 9,127,072 and U.S. Pat. Pub. 2012/0164150 (of Xu & Esmon) disclose a mAb (HAPC1573) that binds to activated protein C and inhibits anticoagulant activity but does not bind to or inhibit activation of unactivated protein C. The documents contemplate other mAbs such as an antibody that inhibits activated or non-activated protein C binding of EPCR. However, nowhere do they state that this is an Ab specific for EPCR (as opposed to being specific for Protein C or APC). Indeed, para [0018] of the '683 publication states that:

> . . . certain methods of the present invention contemplate a method of inhibiting activation of unactivated protein C activation comprising administering to a subject an effective amount of the monoclonal antibody of the present invention. Antibodies employed in such methods may also inhibit activated or unactivated protein C binding of endothelial cell protein C receptor (EPCR) . . . "

None of the above four Xu & Esmon patent references specifically mention hemorrhagic arthropathy.

U.S. Pat. No. 9,657,111 (Zhao et al.) discloses the same mAb HAPC1573 disclosed in the publications of Xu and Esmon above, which recognizes APC, but not unactivated protein C. This facilitated APC internalization on endothelium and could be blocked by either EPCR blocking Ab or Gla domain blocking Ab. The document suggested that the interaction of the mAb and APC prevented APC from cleaving Factor Va and noted that recent studies by others showed that anticoagulant activity of APC is dispensable for its cytoprotective function though this effect of APC was found not only in endothelial cells which express EPCR, but also on other cell types which do not express EPCR on their surfaces. This reference does not mention hemophilia or its attendant hemorrhagic arthropathy.

Korte et al. *Transfus Med Hemother.* 2018, discloses various new approaches for treating Hemophilia A and B including by improving the pharmacokinetics of clotting factor concentrates by prolonging their respective biological half-lives. The document mentions once reducing the negative impact of hemophilia on morbidity ("especially arthropathy"), but there is no mention of EPCR or anti-EPCR antibodies nor treatment aimed specifically at hemorrhagic arthropathy. Moreover, this reference is unavailable as prior art because of its publication date.

None of the foregoing references discloses the present invention (prevention, treatment, etc. of hemorrhagic arthropathy of hemophilia with an anti-EPCR Ab/mAb.

SUMMARY OF THE INVENTION

The present inventors found that an antibody against endothelial cell protein C receptor (EPCR) promoted hemostasis and was highly effective in preventing or reducing the severity of hemophilic arthropathy in a murine model. Their studies were conducted using either a saphenous vein mouse bleeding model or a hemarthrosis model (see Example I and FIGS. 11-14).

The inventors conceived that inhibition of EPCR function by a blocking antibody (or by certain other EPCR binding agents) can be used prophylactically to prevent arthropathy in hemophilia patients and probably in other patient groups, or at least to diminish the symptoms of arthropathy.

Currently, hemophilia is treated by infusing one or more missing or non-functional clotting factors. This has been accomplished by giving plasma, or, more recently, purified or recombinant forms of the clotting factor proteins. (See FIG. 4). Frequent and regular exposure to FVIII (or FIX), often at high doses over the course of months to years may induce immune responses (antibodies) in about 30% of patients (see FIG. 4) which require immunosuppression or immunomodulation (such as immunotolerance induction). It is possible to bypass the FVIII and FIX pathway and avoid such immune-based interference by treating with recombinant FVIIa, thereby bypassing the use of the above clotting factors (see FIG. 5).

The present invention utilizes antibodies against EPCR to achieve a procoagulant effect in hemophilia patient, and as a result to prevent, treat, slow the progression of, or reduce the severity of symptoms of hemophilic arthropathy. This differs from the prior art in that it relies upon antibody treatment rather than replacement of missing or non-functional clotting factors. Antibodies are less expensive to generate, are very stable with a much longer half-life in vivo compared to clotting enzymes. Thus the use of antibody treatment reduces the cost and increases adherence because antibodies can be used, for example, once a week and administered subcutaneously.

Specifically, the present invention provides a method for
  (a) reducing, attenuating or preventing joint swelling, macrophage infiltration, iron deposition and/or blood vessel formation (angiogenesis; neoangiogenesis) in a joint, preferably a knee joint, of a hemophilic mammalian subject, preferably a human; and.
  (b) treating hemophilic arthropathy in a mammalian subject, preferably a human, suffering from hemophilia, comprising administering to said subject an effective amount of an antibody specific for Endothelial Protein C Receptor (EPCR). The antibody is preferably a monoclonal (mAb). Preferred mAbs specific for human EPCR that are "blocking Abs" include JRK 1494 and JRK 1535. Non-blocking mAbs specific for human EPCR—which are useful as controls—are: JRK 1500, and JRK 1513. See Ghosh et al., supra, Nayak, R C et al., *Blood.* 2009, 114(9): 1974-86; Stearns-Kurosawa D J, et al., *Proc Natl Acad Sci USA.* 1996; 93(19):10212-16; Liaw, P C Y et al., *J Biol Chem* 2001; 276, 8364-70.

In the above method, the antibody is preferably in the form of a pharmaceutical composition that further comprises a pharmaceutically acceptable vehicle or excipient, preferably formulated for subcutaneous (SC) administration. Preferably, the antibody or the pharmaceutical composition comprising the antibody is administered by SC injection.

The above method may further comprise administration to the subject of an effective amount of recombinant factor VIIa (rVIIa), preferably comprised in excipient or vehicle suitable for intravenous (IV) administration; preferably the rVIIa is administered intravenously (IV).

The invention is also directed to use of a blocking antibody specific for human EPCR for:
  (a) reducing, attenuating or preventing joint swelling, macrophage infiltration, iron deposition and/or blood vessel formation (angiogenesis; neoangiogenesis) in a joint, preferably a knee joint, of a hemophilic mammalian subject, preferably a human; and
  (b) treatment of hemophilic arthropathy in the subject.

Also provided is the use of a blocking antibody specific for EPCR, for the manufacture of a medicament for:
  (a) reducing, attenuating or preventing joint swelling, macrophage infiltration, iron deposition and/or blood vessel formation (angiogenesis; neoangiogenesis) in a joint, preferably a knee joint, of a hemophilic mammalian subject, preferably a human; and
  (b) treatment of hemophilic arthropathy in the subject.

DESCRIPTION OF THE PREFERRED EMBODIMENTS

Figure 1:
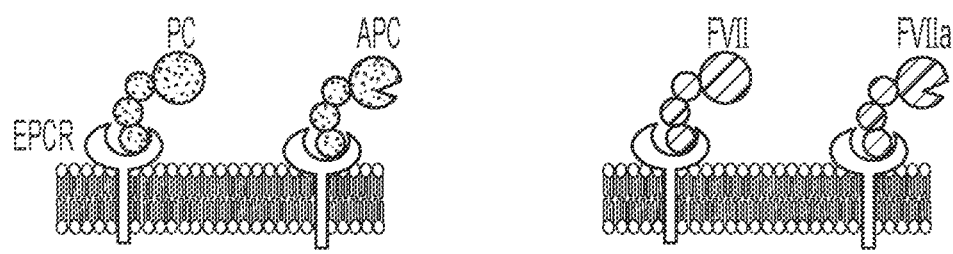
FIG. 1 is a 'cartoon' showing the binding of protein C (PC), activated PC (APC), clotting factors FVII and FVIIa bound to the EPCR embedded in the cell membrane. EPCR is homologous to the MHC class 1/CD1 family, members of which contain two α-helices that sit upon an 8-stranded (3-sheet platform. Ten residues that, when mutated to alanine, result in the loss of protein C/APC binding ($Arg^{81}$, $Leu^{82}$, $Val^{83}$, $Glu^{86}$, $Arg^{87}$, $Phe^{146}$, $Tyr^{154}$, $Thr_{157}$, $Arg^{158}$, and $Glu^{160}$). Also shown are the amino acid residues important for this binding to the EPCR. See, e.g., Liaw, et al., supra.
Figure 2:
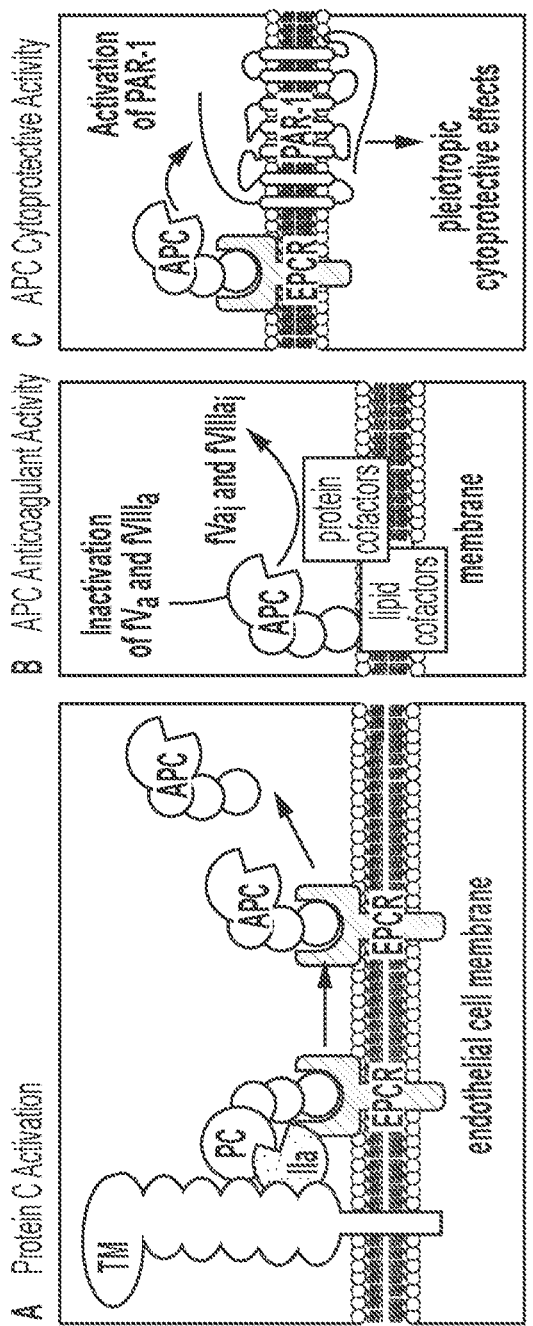
FIG. 2A-C is a set of cartoons showing (A) the activation of PC to APC after binding to cell surface EPCR; (B) the anticoagulant activity of APC (and inactivation of FV and FVIII; and (C) the pleiotropic cytoprotective actions of APC, including the activation of PAR1
Figure 3:
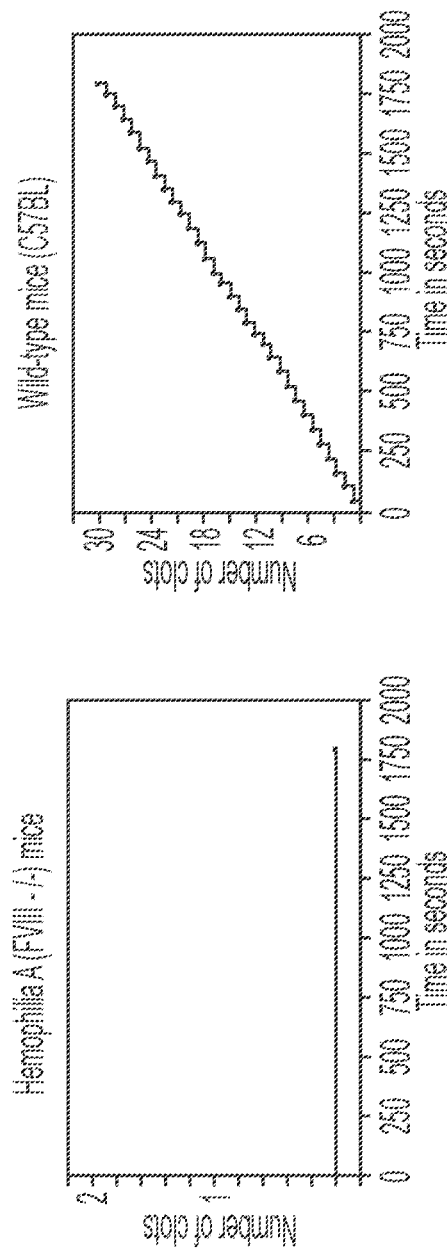
FIG. 3 shows two graphs comparing blood clotting in Wild type C57BL mice FVIII−/− knockout mice modeling Hemophilia A.
Figure 4:
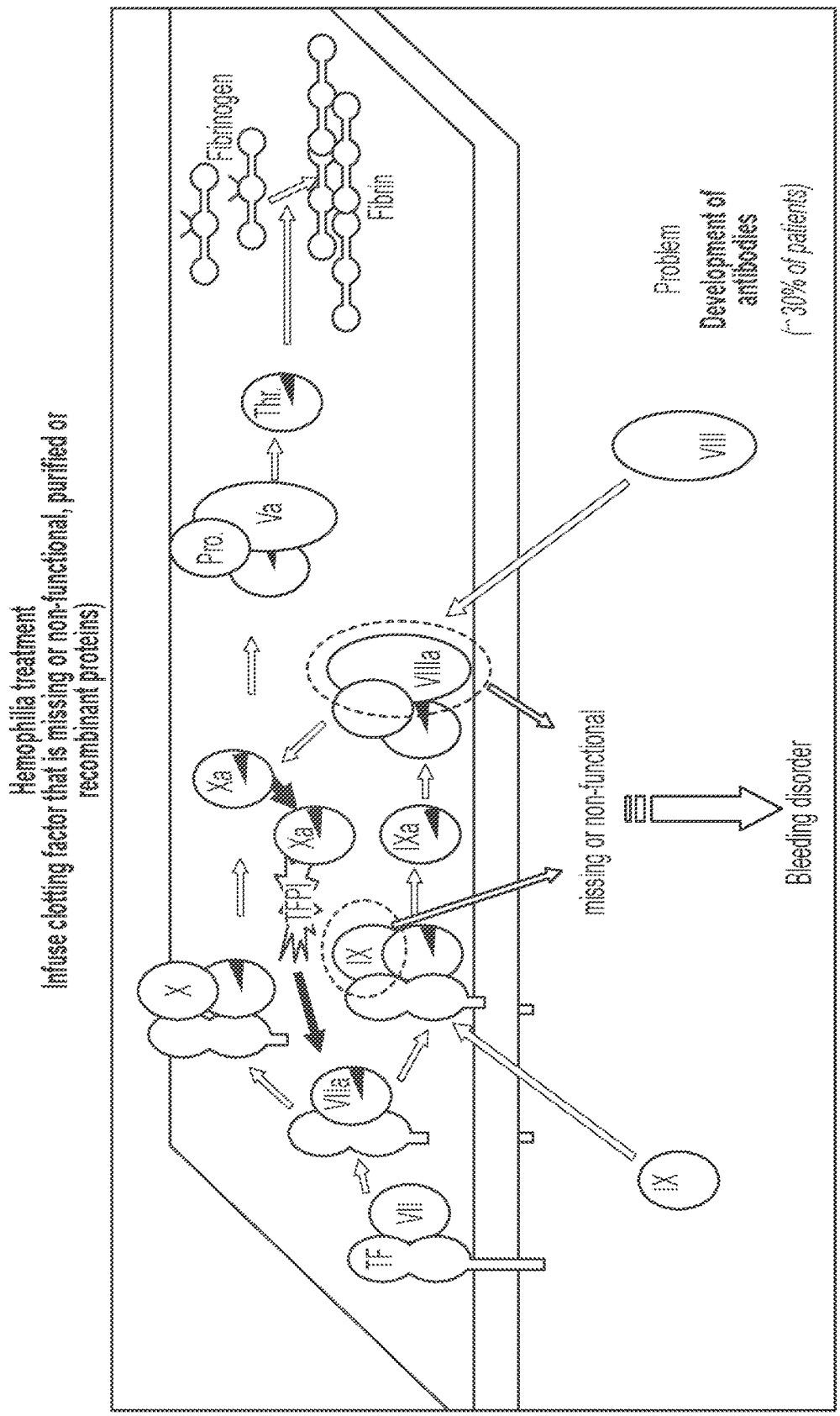
FIG. 4 is a cartoon/schematic showing the basis of certain bleeding disorders and indicating the problem of antibody development to treatment by replacing FVIII or FIX.
Figure 5:
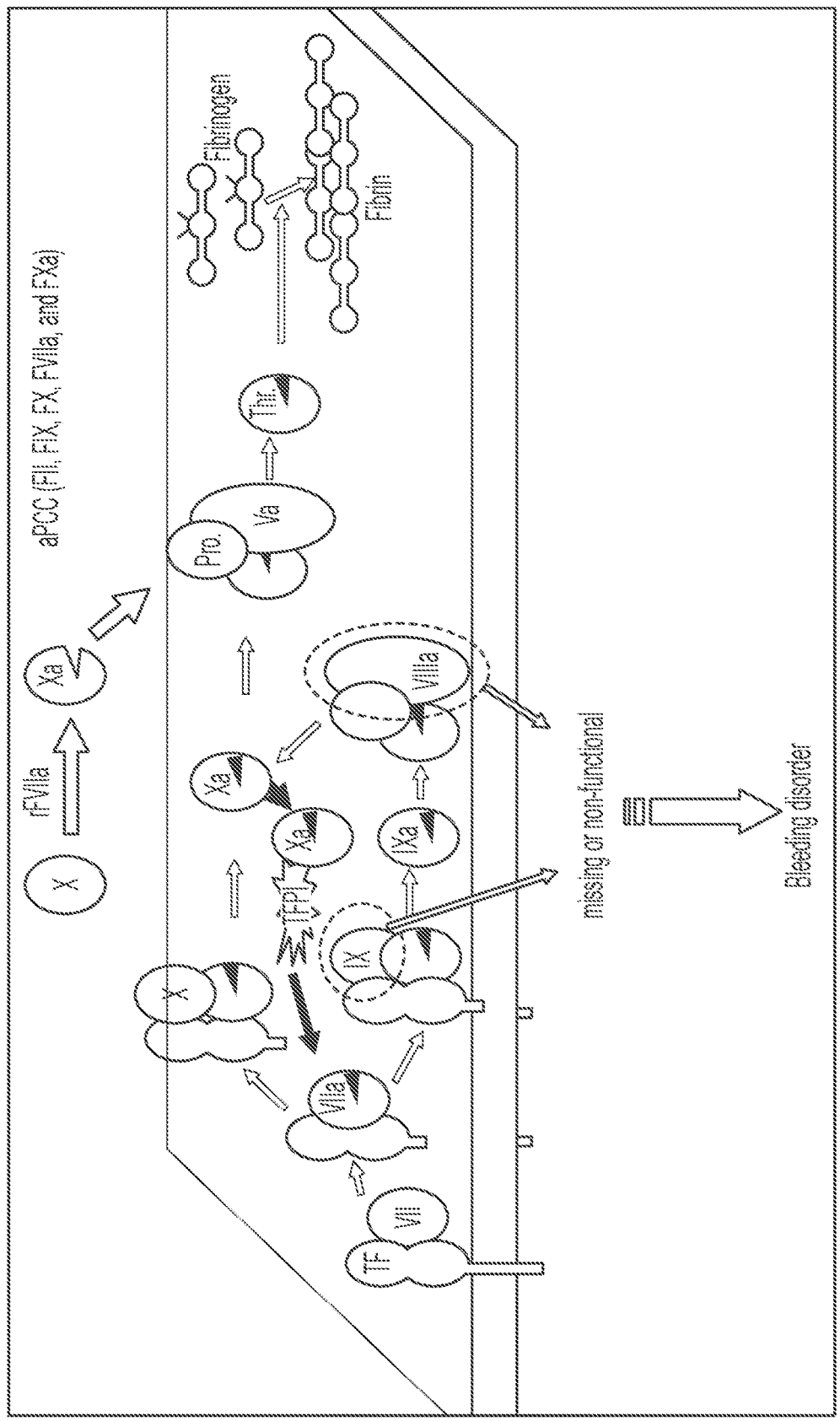
FIG. 5 is a cartoon/schematic describing the treatment of hemophiliacs with inhibitors, specifically bypassing agents, such as recombinant FVIIa (rFVIIa).
Figure 6:
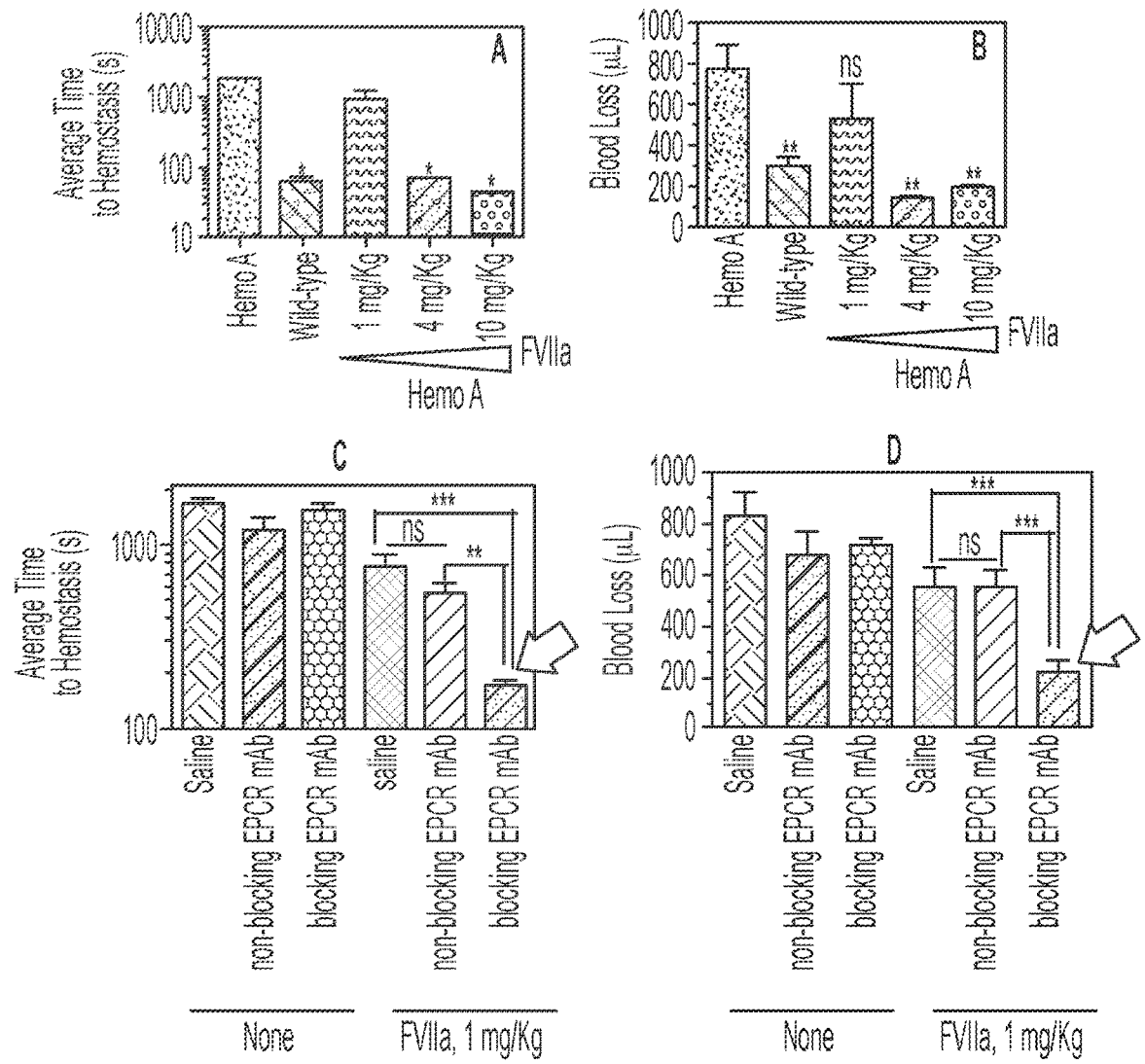
FIG. 6A-D is a series of 4 graphs showing that low dose FVIIa corrects bleeding in hemophilia A mice when EPCR blocking mAb were administered. (A) and (C) show "time to hemostasis" and (B) and (D) show blood loss. (C) and (D) show the potent effect of adding "blocking" EPCR mAbs to a low, ineffective dose of FVIIa (1 mg/kg).

The present invention is a result of the discovery that a class of anti-EPCR antibodies referred to as blocking antibodies are effective for treating or preventing the development of arthropathy in hemophilic subjects as well as reducing, attenuating or preventing various biological reactions associated with arthropathy, including educing joint swelling, macrophage infiltration, iron deposition and/or blood vessel formation (angiogenesis; neoangiogenesis). Such antibodies are therefore novel therapeutics for treating hemophilia patients, particularly those with arthropathy.

By the term "treating" is intended the administering to a subject of a composition comprising a blocking anti-EPCR antibody as described herein or an EPCR-binding homologue polypeptide, amino acid substitution variant, or a small molecular inhibitor thereof that maintains the ability to bind to and block EPCR (as does the Ab), alone or in combination. These agents may be administered concurrently or sequentially. A pharmaceutical composition comprises such a composition in a pharmaceutically acceptable vehicle. "Treatment" as used herein is not meant to imply or require total prevention of or disappearance hemophilic arthropathy. "Treatment" or "treating" is also intended to include prophylaxis, i.e., the prevention or reduction of development the arthropathy in any one or more joints of the subject. Also intended is the use of the present methods in conjunction with other known/conventional hemophilia treatments, including administration of, for example, rVIIa. When used as a supplemental treatment, the method of the present invention can be initiated before the start of conventional treatment, continued during intervals between subsequent recurring rounds of conventional therapy, and may be continued after cessation of conventional therapy.

Administration of the compositions of the present invention may be by parenteral, subcutaneous (SC), intravenous (IV), intramuscular, intraperitoneal, transdermal routes, preferably by the SC route.

The dosage administered will be dependent upon the age, health, and weight of the recipient, kind of concurrent treatment, if any, frequency of treatment, and the nature of the effect desired.

Compositions within the scope of this invention include compositions comprising an anti-EPCR antibody, preferably a mAb. The composition is administered in an amount effective to achieve its intended purpose. While individual needs vary, determination of optimal ranges of effective amounts of each component is within the skill of the art. Typical dosages comprise 0.1 to 50 mg/kg/body wt, though more preferred dosages are described for certain particular uses, above and below.

The therapeutic dosage administered is an amount which is therapeutically effective, as is known to or readily ascertainable by those skilled in the art. The dose is also dependent upon the age, health, and weight of the recipient, kind of concurrent treatment(s), if any, the frequency of treatment, and the nature of the effect desired.

Antibodies

The Abs useful in this invention are termed blocking Abs, which means that the Ab blocks protein C or APC binding to the EPCR. Non-blocking Ab means that the Ab binds the EPCR but does not interfere with protein C or APC binding to EPCR.

Blocking antibody inhibits thrombin-thrombomodulin mediated protein C activation while a non-blocking antibody does not. The binding sites of human EPCR important for binding human EPCR blocking and non-blocking mAb appear in Liaw, P C Y et al., supra, incorporated by reference in its entirety. Esmon, C T et al., *Meth Enzymol*. (1993) 22:359-85, describe the production of mAbs against human EPCR using a soluble EPCR fusion protein comprising an N-terminal epitope, a FXa cleavage site followed by EPCR truncated at residue 210.

Preferred anti-human EPCR mAbs with blocking ability include JRK 1494 and JRK 1535 (available, for example, from Sigma-Aldrich). The EPCR epitope recognized by JRK 1494 was localized to amino acid residues $Trp^{26}$ to $Val^{116}$ of human EPCR (hEPCR). The epitope recognized by JRK 1535 was localized to residues $Phe^{113}$ to $Cys^{222}$. The epitope recognized for non-blocking mAb JRK 1500 likely included residues $Arg^{127}$, $Glu^{129}$, and $Arg^{130}$ whereas the stretch of residues $Val^{25}$ to $Leu^{52}$ contains the epitope recognized by nonblocking mAb JRK 1513 (Liaw et al., supra)

Assays useful for determining the blocking or non-blocking abilities are known in the art and/or disclosed herein. For example, transiently transfected 293T cells are screened for the ability to bind fluorescein isothiocyanate ("FL")-labeled anti-human EPCR mAb, Blocking mAbs block hEPCR/FL-APC interactions, whereas nonblocking mAbs do not. As expected, protein C also blocks hEPCR/FL-APC interactions (Regan, L et al., *J. Biol. Chem.* 1997; 272:26279-284). The effect of the above four mAbs (blocking and nonblocking) on the interaction between hEPCR and FL-protein C is identical to that observed on the interaction between hEPCR and FL-APC (Liaw et al., supra)

Mouse mAbs against human EPCR (JRK-1494/blocking mAb and JRK-1500/nonblocking mAb) were prepared as described by Stearns-Kurosawa D J, et al., supra. mAbs against mouse EPCR (mAb 1560/blocking mAb and mAb 1567/nonblocking mAb) were prepared by immunizing rats with recombinant mouse soluble EPCR (Li W et al., *Thromb Haemost.* 2005; 3(7):1351-59). Other useful anti-human EPCR include RCR-252 (rat) from various source, e.g., Novus Biologicals, MyBiosource;

Monoclonal antibodies (mAbs) and methods for their production and use are described in Kohler and Milstein, *Nature* 256:495-497 (1975); U.S. Pat. No. 4,376,110; Hartlow, E. et al., *Antibodies: A Laboratory Manual*, Cold Spring Harbor Laboratory Press, Cold Spring Harbor, NY, 1988); *Monoclonal Antibodies and Hybridomas: A New Dimension in Biological Analyses*, Plenum Press, New York, NY (1980); H. Zola et al., in *Monoclonal Hybridoma Antibodies: Techniques and Applications*, CRC Press, 1982)).

Immunoassay methods are also described in Coligan, J E et al., eds., *Current Protocols in Immunology*, Wiley-Interscience, New York 1991 (or current edition); Butt, WR (ed.) *Practical Immunoassay: The State of the Art*, Dekker, New York, 1984; Bizollon, C A, ed., *Monoclonal Antibodies and New Trends in Immunoassays*, Elsevier, New York, 1984; Butler, J E, ELISA (Chapter 29), In: van Oss, C J et al., (eds), *IMMUNOCHEMISTRY*, Marcel Dekker, Inc., New York, 1994, pp. 759-803; Butler, J E (ed.), *Immunochemistry of Solid-Phase Immunoassay*, CRC Press, Boca Raton, 1991; Weintraub, B, *Principles of Radioimmunoassays*, The Endocrine Society, March, 1986; Work, T S et al., *Laboratory Techniques and Biochemistry in Molecular Biology*, North Holland Publishing Company, NY, 1978; Dabbs, D J, *Diagnostic Immunohistochemistry*, Churchill Livingstone, 2001.

The present invention provides antibodies, both polyclonal and monoclonal, preferably mAbs reactive with EPCR, preferably human EPCR. The antibodies may be xenogeneic, allogeneic, syngeneic, or modified forms thereof, such as humanized or chimeric antibodies. The term "antibody" is also meant to include both intact molecules as well as fragments thereof that include the antigen-binding site and are capable of binding to a relevant target epitope of EPCR. These include Fab and F(ab')$_2$ fragments which lack the Fc fragment of an intact Ab, clear more rapidly from the circulation, and may have less non-specific tissue binding than an intact Ab (Wahl et al., *J. Nucl. Med.* 24:316-25 (1983)). Also included are Fv fragments (Hochman, J. et al. (1973) *Biochemistry* 12:1130-35; Sharon, J. et al. (1976) Biochemistry 15:1591-94).). These various fragments are produced using conventional techniques such as protease cleavage or chemical cleavage (see, e.g., Rousseaux et al., *Meth. Enzymol.*, 121:663-69 (1986))

Polyclonal antibodies are obtained as sera from immunized animals such as rabbits, goats, rodents, etc. and may be used directly without further treatment or may be subjected to conventional enrichment or purification methods such as ammonium sulfate precipitation, ion exchange chromatography, and affinity chromatography (see Zola et al., supra).

An immunogen for the generation of the antibodies of this invention may comprise EPCR or an epitope-bearing fragment(s) or derivative thereof. Useful immunogens are produced in a variety of ways known in the art, e.g., expression of cloned genes using conventional recombinant methods, isolation from cells of origin, cell populations expressing high levels of EPCR, etc. In the case of shorter fragments, they may be chemically synthesized.

The mAbs may be produced using conventional hybridoma technology, such as the procedures introduced by Kohler and Milstein (*Nature*, 256:495-97 (1975)), and modifications thereof (see above references). Hybridomas produced according to these methods can be propagated in vitro or in vivo (in ascites fluid) using techniques known in the art (see generally Fink et al., *Prog. Clin. Pathol.*, 9:121-33 (1984)). Generally, the individual cell line is propagated in culture, and the culture medium containing high concentrations of a single mAb can be harvested by decantation, filtration, or centrifugation.

Test Cells for Screening and Characterizing Antibodies

Pure EPCR immobilized onto plastic may be used for the primary screening. Cells that have been engineered to overexpress EPCR may also be used to demonstrate cell binding of an anti-EPCR mAb. In one embodiment, a hybridoma supernatant (e.g., 50 µl) is added to wells containing fixed EPCR-expressing cells for about 1.5 h at 37° C. Plates are washed twice in washing buffer (such as PBS/0.05% Tween-20), and Rhodamine Red-conjugated goat anti-mouse IgG is added (e.g., 30 µl/well) at an appropriate dilution, such as 1:100, for 1.5 h at 37° C. After washing in a washing buffer, cells are examined for the presence of immunofluorescence; in the embodiment described here, fluorescence microscopy is used.

In this embodiment, immunofluorescence is the basis for determining whether a hybridoma supernatant contains an Ab specific for the EPCR (although immunohistochemical staining may also be used). If supernatants show positively staining the hybridoma clones are selected, expanded and the supernatants tested for reactivity to the complex by ELISA.

The term "antibody" is meant to include both intact immunoglobulin (Ig) molecules as well as fragments and derivative thereof, that may be produced by proteolytic cleavage of Ig molecules or engineered genetically or chemically. Fragments include, for example, Fab, Fab', F(ab')$_2$ and Fv, each of which is capable of binding antigen. These fragments lack the Fc fragment of intact Ab and have an additional advantage, if used therapeutically, of clearing more rapidly from the circulation and undergoing less non-specific tissue binding than intact antibodies. Papain treatment of Ig's produces Fab fragments; pepsin treatment produces F(ab')$_2$ fragments. These fragments may also be produced by genetic or protein engineering using methods well known in the art. A Fab fragment is a multimeric protein consisting of the portion of an Ig molecule containing the immunologically active portions of an Ig heavy (H) chain and an Ig light (L) chain covalently coupled together and capable of specifically combining with antigen. Fab fragments are typically prepared by proteolytic digestion of substantially intact Ig molecules with papain using methods that are well known in the art. However, a Fab fragment may also be prepared by expressing in a suitable host cell the desired portions of Ig H chain and L chain using methods well known in the art. A (Fab')$_2$ fragment is a tetramer that includes a fragment of two H and two L chains. The Fv fragment is a multimeric protein consisting of the immunologically active portions of an Ig H chain variable (V) region ($V_H$) and an Ig L chain V region ($V_L$) covalently coupled together and capable of specifically combining with antigen. Fv fragments are typically prepared by expressing in suitable host cell the desired portions of Ig $V_H$ region and $V_L$ region using methods well known in the art.

Single-chain antigen-binding protein or single chain Ab, also referred to as "scFv," is a polypeptide composed of an Ig $V_L$ amino acid sequence tethered to an Ig $V_H$ amino acid sequence by a peptide that links the C-terminus of the $V_L$ sequence to the N-terminus of the $V_H$ sequence.

As noted, in a preferred embodiment, the Ab is mAb designated JRK 1494 or JRK 1535.

Chimeric Antibodies

The chimeric antibodies of the invention comprise individual chimeric H and L Ig chains. The chimeric H chain comprises an antigen binding region derived from the H chain of a non-human Ab specific for e.g., EPCR, which is linked to at least a portion of a human $C_H$ region. A chimeric L chain comprises an antigen binding region derived from the L chain of a non-human Ab specific for the target antigen linked to at least a portion of a human $C_L$ region. As used herein, the term "antigen binding region" refers to that portion of an Ab molecule which contains the amino acid residues that interact with an antigen and confer on the Ab its specificity and affinity for the antigen. The Ab region includes the "framework" amino acid residues necessary to maintain the proper conformation of the antigen-binding (or "contact") residues.

As used herein, the term "chimeric antibody" includes monovalent, divalent or polyvalent Igs. A monovalent chimeric Ab is an HL dimer formed by a chimeric H chain associated through disulfide bridges with a chimeric L chain. A divalent chimeric Ab is tetramer $H_2L_2$ formed by two HL dimers associated through at least one disulfide bridge. A polyvalent chimeric Ab can also be produced, for example, by employing a $C_H$ region that aggregates (e.g., from an IgM H chain, termed the µ chain).

Antibodies, fragments or derivatives having chimeric H chains and L chains of the same or different V region binding specificity, can be prepared by an appropriate association of the individual polypeptide chains, as taught, for example by Sears et al., Proc. Natl. Acad. Sci. USA 72:353-357 (1975). With this approach, hosts expressing chimeric H chains (or their derivatives) are separately cultured from hosts expressing chimeric L chains (or their derivatives), and the Ig chains are separately recovered and then associated. Alternatively, the hosts can be co-cultured and the chains allowed to associate spontaneously in the culture medium, followed by recovery of the assembled Ig, fragment or derivative.

The antigen binding region of the chimeric Ab (or a human mAb) of the present invention is derived preferably from a non-human Ab specific EPCR. The non-human Ab producing cell from which the V region of the Ab of the invention is derived may be a B lymphocyte obtained from the blood, spleen, lymph nodes or other tissue of an animal immunized with EPCR or a relevant epitope thereof. The Ab-producing cell contributing the nucleotide sequences encoding the antigen-binding region of the chimeric Ab of the present invention may also be produced by transformation of a non-human, such as a primate, or a human cell. For example, a B lymphocyte (Kozbor et al. Immunol. Today 4:72-79 (1983)). Alternatively, the B lymphocyte may be transformed by providing a transforming gene or transforming gene product, as is well-known in the art. Preferably, the antigen binding region will be of murine origin. In other embodiments, the antigen binding region may be derived from other animal species, in particular, rodents such as rat or hamster.

The murine or chimeric mAb of the present invention may be produced in large quantities by injecting hybridoma or transfectoma cells secreting the Ab into the peritoneal cavity of mice and, after an appropriate time, harvesting the ascites fluid which contains a high titer of the mAb. Alternatively, the antibodies may be produced by culturing hybridoma (or transfectoma) cells in vitro and isolating secreted mAb from the cell culture medium.

Human genes which encode the constant C regions of the chimeric antibodies of the present invention may be derived from a human fetal liver library or from any human cell including those which express and produce human Igs. The human $C_H$ region can be derived from any of the known classes or isotypes of human H chains, including γ, µ, α, δ or ε, and subtypes thereof, such as G1, G2, G3 and G4. Since the H chain isotype is responsible for the various effector functions of an Ab, the choice of $C_H$ region will be guided by the desired effector functions. Preferably, the $C_H$ region is derived from γ1 (IgG1), γ3 (IgG3), γ4 (IgG4), or µ (IgM). The human $C_L$ region can be derived from either human L chain isotype, κ or λ.

Genes encoding human Ig C regions are obtained from human cells by standard cloning techniques (Sambrook, J. et al., *Molecular Cloning: A Laboratory Manual,* 2nd Edition, Cold Spring Harbor Press, Cold Spring Harbor, NY (1989)). Human C region genes are readily available from known clones containing genes representing the two classes of L chains, the five classes of H chains and subclasses thereof. Chimeric Ab fragments, such as $F(ab')_2$ and Fab, can be prepared by designing a chimeric H chain gene which is appropriately truncated. For example, a chimeric gene encoding an H chain portion of an $F(ab')_2$ fragment would include DNA sequences encoding the $CH_1$ domain and hinge region of the H chain, followed by a translational stop codon to yield the truncated molecule.

The chimeric Ig coding sequences or genes of the present invention can also be expressed in nonlymphoid mammalian cells or in other eukaryotic cells, such as yeast, or in prokaryotic cells, in particular bacteria. Yeast provides substantial advantages over bacteria for the production of Ig H and L chains. Yeasts carry out post-translational peptide modifications including glycosylation. A number of recombinant DNA strategies now exist which utilize strong promoter sequences and high copy number plasmids which can be used for the production of the desired proteins in yeast. Yeast recognizes leader sequences of cloned mammalian gene products and secretes peptides bearing leader sequences (i.e., pre-peptides). Yeast gene expression systems can be routinely evaluated for the levels of production, secretion and the stability of chimeric H and L chain proteins and assembled chimeric Abs. Any of a series of yeast gene expression systems incorporating promoter and termination elements from the actively expressed genes coding for glycolytic enzymes produced in large quantities when yeasts are grown in media rich in glucose can be utilized. Bacterial strains may also be utilized as hosts for the production of Ab molecules or Ab fragments described by this invention. Preferred hosts are mammalian cells, grown in vitro or in vivo. Mammalian cells provide post-translational modifications to Ig protein molecules including leader peptide removal, folding and assembly of H and L chains, glycosylation of the Ab molecules, and secretion of functional Ab protein. Mammalian cells which may be useful as hosts for the production of Ab proteins, in addition to the cells of lymphoid origin described above, include cells of fibroblast origin, such as Vero (ATCC CRL 81) or CHO-K1 (ATCC CRL 61). Many vector systems are available for the expression of cloned H and L chain genes in mammalian cells (see Glover, supra). Different approaches can be followed to obtain complete $H_2L_2$ Abs.

For in vivo use, particularly for injection into humans, it is desirable to decrease the immunogenicity of the mAb by making mouse-human (or rodent-human) chimeric Abs as above, or by humanizing the Abs using methods known in the art. The humanized Ab may be the product of an animal having transgenic human Ig Constant region genes (see for example WO90/10077 and WO90/04036). Alternatively, the Ab of interest may be genetically engineered to substitute the $CH_1$, $CH_2$, $CH_3$, hinge domains, and/or the framework domain with the corresponding human sequence (see WO92/02190).

Single Chain Antibodies

The Ab of the present invention may be produced as a single chain Ab or scFv instead of the normal multimeric structure. Single chain Abs include the hypervariable regions from an Ig of interest and recreate the antigen binding site of the native Ig while being a fraction of the size of the intact Ig (Skerra, A. et al. (1988) *Science,* 240: 1038-1041; Pluckthun, A. et al. (1989) *Methods Enzymol.* 178: 497-515; Winter, G. et al. (1991) *Nature,* 349: 293-299); Bird et al., (1988) *Science* 242:423; Huston et al. (1988) *Proc. Natl. Acad. Sci. USA* 85:5879; Jost C R et al., *J Biol Chem.* 1994 269:26267-26273; U.S. Pat. Nos. 4,704,692, 4,853,871, 4,94,6778, 5,260,203, 5,455,030). DNA sequences encoding the V regions of the H chain and the L chain are ligated to a linker encoding at least about 4 amino acids (typically small neutral amino acids). The protein encoded by this fusion allows assembly of a functional variable region that retains the specificity and affinity of the original Ab.

Antibodies can be selected for particular desired properties. In the case of an Ab to be used in vivo, Ab screening procedures can include any of the in vitro or in vivo bioassays that measure binding to EPCR, to cells expressing the relevant polypeptide or peptide epitope.

Pharmaceutically Compositions

In addition to a pharmacologically active Ab, the present pharmaceutical compositions/preparations preferably contain suitable pharmaceutically acceptable carriers comprising excipients and auxiliaries which facilitate the processing of the active compounds into preparations which can be used pharmaceutically as is well known in the art. Suitable solutions for administration by injection, may contain from about 0.01 to 99 percent, active compound(s) together with the excipient.

The pharmaceutical compositions of the present invention are manufactured in a manner which is itself known, for example, by means of conventional mixing, granulating, dissolving, or lyophilizing processes. Suitable excipients may include fillers binders, disintegrating agents, auxiliaries and stabilizers, all of which are known in the art. Suitable formulations for parenteral administration include aqueous solutions of the Ab in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension.

The pharmaceutical formulation for systemic administration according to the invention may be formulated for parenteral administration and various types of the formulation may be used simultaneously to achieve systemic administration of the active ingredient.

Other pharmaceutically acceptable carriers the present composition are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension.

The hydrophobic layer, or lipidic layer, generally, but not exclusively, comprises phospholipids such as lecithin and sphingomyelin, steroids such as cholesterol, more or less ionic surface active substances such as dicetylphosphate, stearylamine or phosphatidic acid, and/or other materials of a hydrophobic nature.

The methods of this invention may be used to inhibit growth or metastasis of MPM in a subject in need thereof. The active nucleic acid/expression vector, protein, peptide or small organic molecule or pharmaceutically acceptable salt thereof is preferably administered in the form of a pharmaceutical composition as described above.

Doses preferably include pharmaceutical dosage units comprising an effective amount of the therapeutic agent. Dosage unit form refers to physically discrete units suited as unitary dosages for a mammalian subject; each unit contains a predetermined quantity of active material calculated to produce the desired therapeutic effect, in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active compound for the treatment of, and sensitivity of, individual subjects By an effective amount is meant an amount sufficient to achieve a regional concentration or a steady state systemic concentration in vivo, which results in a measurable reduction in any relevant parameter of disease.

The amount of antibody to be administered depends on the antibody that is selected, the state of the disease or condition, the route of administration, the health and weight of the recipient, the existence of other concurrent treatment, if any, the frequency of treatment, the nature of the effect desired, and the judgment of the skilled practitioner.

A preferred single dose, given once daily for treating a subject, preferably a mammal, more preferably human who his suffering from hemophilia and is suffering from or is susceptible to hemophilic arthropathy is between about 0.1 mg/kg and about 50 mg/kg, preferably between about 0.5 mg/kg and about 5 mg/kg, for example. Such a dose can be administered daily for anywhere from about 3 days to one or more weeks. Chronic administration is also possible, though the dose may need to be adjusted downward. The foregoing ranges are, however, suggestive, as the number of variables in an individual treatment regime is large, and considerable excursions from these preferred values are expected.

Effective doses and optimal dose ranges may be determined in vitro or in vivo using methods well-known in the art, including the method described herein.

Having now generally described the invention, the same will be more readily understood through reference to the following examples which are provided by way of illustration, and are not intended to be limiting of the present invention, unless specified.

Example I

Materials and Methods

Mice
Wild-type (WT) mice of the C57BL/6J (B6) strain were obtained from Jackson Laboratories (Bar Harbor, ME) as were FVIII$^{-/-}$ in B6×129 mice. The latter strain had backcrossed B6 mice for more than 10 generations to generate FVIII$^{-/-}$ mice on the B6 genetic background.
Antibody-Induced Hemophilia:
B6 mice were administered FVIII Ab (1 mg/kg) one to two hours prior to inducing bleeding. The antibody neutralizes 90 to 95% of FVIII clotting activity and induces a hemophilic condition. See: Keshava et al., "Factor VIIa interaction with EPCR modulates the hemostatic effect of rFVIIa in hemophilia therapy: Mode of its action. *Blood Advances.* 2017; 1(15):1206-14.
Hemarthrosis Study Design
The method is described by Hakobyan, N., et al. (2016) "Haemarthrosis model in mice: BSS—Bleeding Severity Score assessment system." *Haemophilia* 22(5): 790-798. Needle puncture was used to induce hemarthrosis, in which a 30 gauge needle was inserted between the anterior portions of the femur and tibia. Human rFVIIa or EPCR mAb (1 mg/kg body wt. were used
Dose schedule:
   Day 0: inject FVIIa or EPCR mAb
     or
   Day 1 and 3; inject FVIIa EPCR mAb
   Day 14 Euthanize, collect blood and fix knee joints for analyses
Analysis of the Extent of Injury
The method of Valentino L A and Hakobyan ("Histological changes in murine haemophilic synovitis: a quantitative grading system to assess blood-induced synovitis, *Haemophilia.* 2006 12(6):654-629 was used to assess
  1. Diameter of knee
  2. Visual bleeding
  3. Synovitis
After review of over 1000 histological sections, six characteristic changes were identified and graded according to Valentino L A and Hakobyan, "Histological changes in murine haemophilic synovitis: a quantitative grading system to assess blood-induced synovitis," *Haemophilia.* 2006 12(6):654-62.
   (i) synovial hyperplasia; (0-3)
   (ii) vascularity; (0-3)
   (iii) discoloration by hemosiderin; (0 or 1).
   (iv) the presence of blood (erythrocytes); (0 or 1).
   (v) villus formation (0 or 1); and
   (vi) cartilage erosion (0 or 2)
   (Maximum Score=11)
Antibodies and Other Reagents
Anti-murine EPCR mAbs (blocking antibody mAb1560 and non-blocking antibody mAb1567) were obtained from Charles Esmon, Oklahoma Medical Research Foundation, Oklahoma City, OK.
Recombinant human FVIIa was obtained from Novo Nordisk (Maaloev, Denmark). All other clotting reagents were obtained from either Enzyme Research Laboratories (South Bend, IN) or Hematological Technologies (Essex Junction, VT).
Statistical Analysis
Statistical significance between the groups was determined by Student's t-test or the nonparametric Mann-Whitney U test. Differences were considered statistically significant if $P<0.05$. All results were expressed as mean±SEM. Statistical comparisons were done using the GraphPad Prism program (GraphPad software).

Example II

Figure 7:
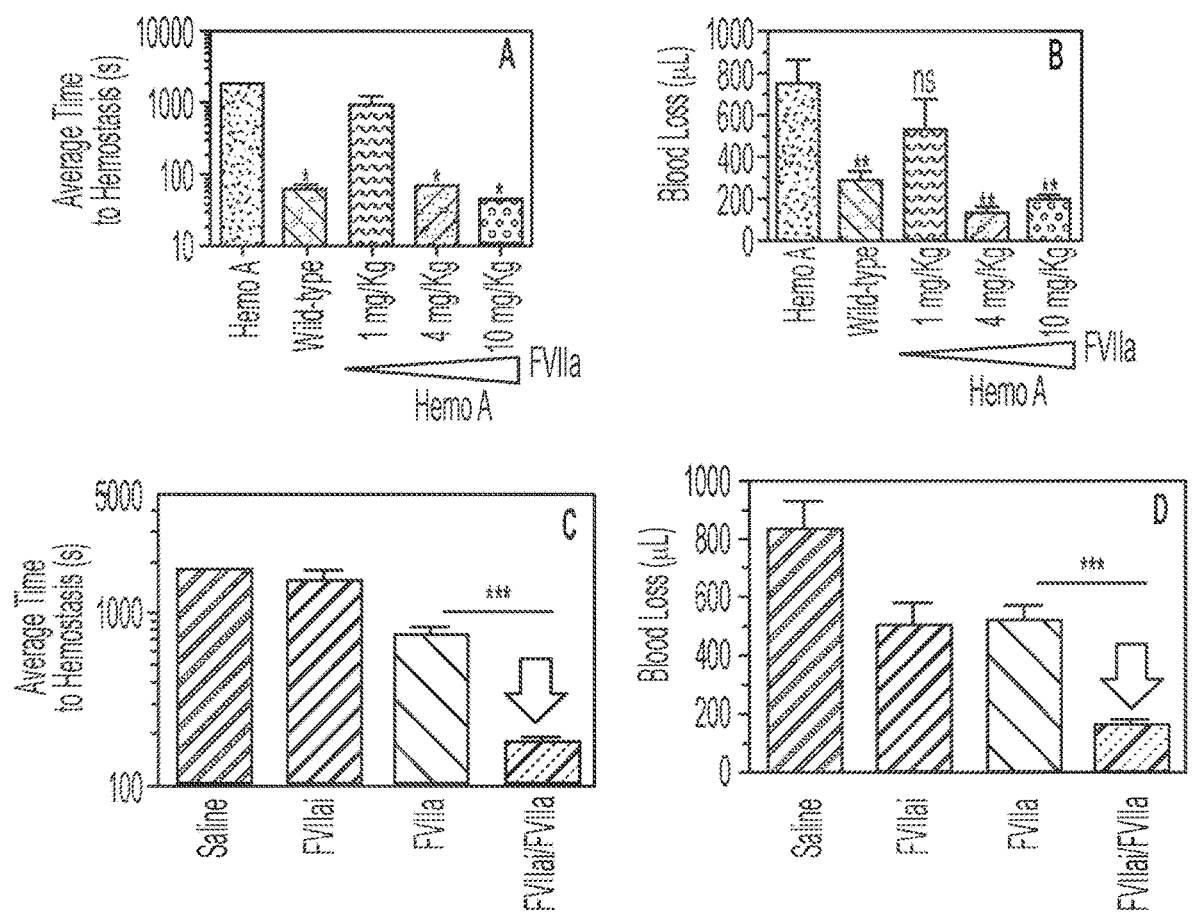
FIG. 7A-D is a series of 4 graphs showing that high concentrations of inactive FVIIa enhances the hemostatic effect of active FVIIa. (A) and (B) are as in FIG. 7. (C) and (D) show the potent effect of adding inactive FVIIa ($FVIIa_i$; at a dose of 10 mg/kg) to active FVIIa (at a dose of 1 mg/kg). Use of this method shows that the blocking of protein C binding to EPCR promotes coagulation, consistent with the results using anti-EPCR mAb. (Both FVIIa and $FVIIa_i$ block protein C binding, but $FVIIa_i$ has no coagulant function).

Correction of Bleeding in Hemophilia A Mice by EPCR Blocking mAb
Subjects were administered the doses of FVIIa and blocking anti-EPCR mAb as described above. The results shown in FIG. 7 indicate that a low dose of FVIIa corrects bleeding in hemophilia A mice when EPCR blocking mAb were also administered

Example III

Inactive FVIIa Enhances the Hemostatic Effect of Active FVIIa

Figure 8:
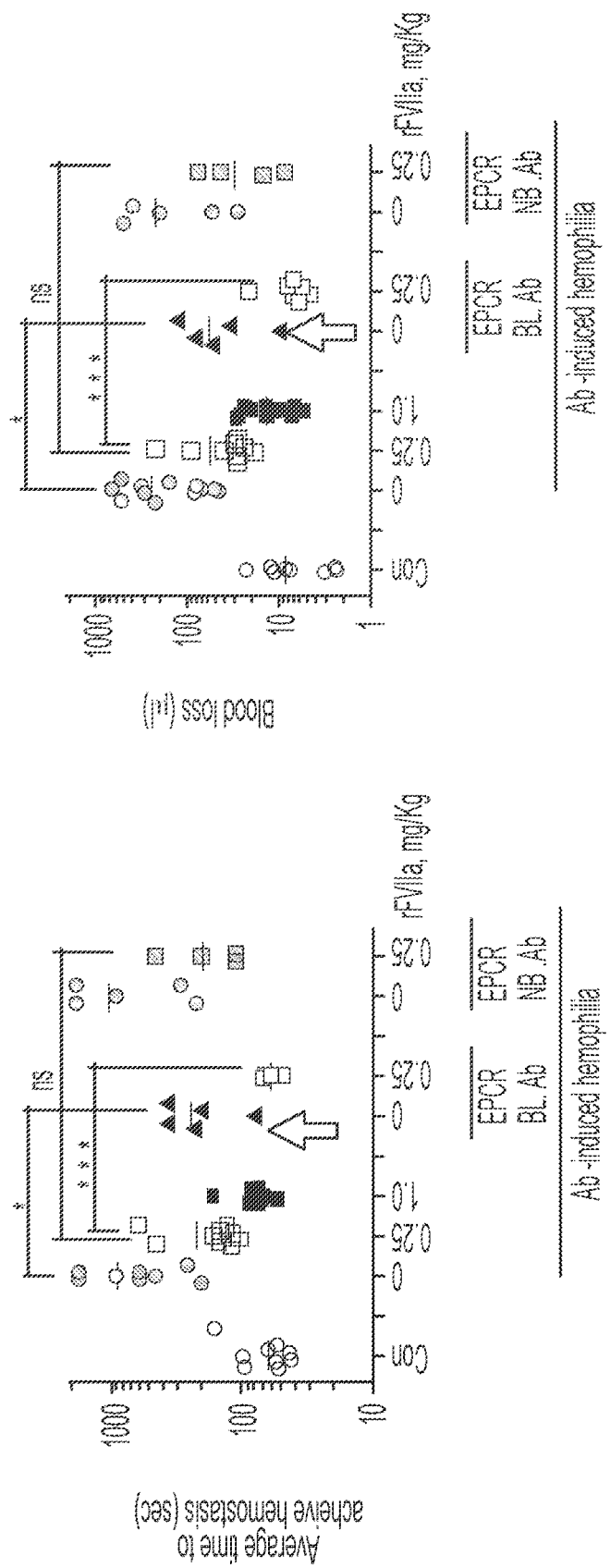
FIG. 8 provides two graphs showing the effect of EPCR mAb on FVIII Ab-induced hemophilia bleeding. Here, the hemophilic condition was induced in wild-type mice by administering anti-FVIII neutralizing antibodies. Left graph shows time to hemostasis; right graph shows blood loss. Abbreviations: EPCR BL.Ab=blocking anti-EPCR Ab; EPCR NB.Ab=non-blocking anti-EPCR Ab. In contrast to untreated animals or those treated with NB.Ab, the mice treated with BL.Ab showed more rapid hemostasis and less blood loss.

Subjects were administered the doses of active and/or inactive FVIIa. The results shown in FIG. 8 indicate that higher doses of FVIIa reduced clotting time and blood loss in hemophilia A mice. When a dose of 10 mg/kg of inactive FVIIa was added to a dose of 1 mg/kg active FVIIa, the reduction in clotting time and in blood loss were greater than with either agent alone.

Example IV

Effect of EPCR mAb on FVIII Ab-Induced Hemophilia Bleeding

Figure 9:
FIG. 9 is a photograph of a knee joint of a human hemophilia patient suffering from arthropathy.

In a model of hemophilia induced by anti-FVIII antibody (see Example I), the results of which are shown in FIG. 9, both the time to hemostasis and the blood loss were reduced significantly by a blocking Ab to EPCR.

Example V

FVIIa or EPCR Antibody Treatment of Hemophilic Arthropathy

Figure 10:
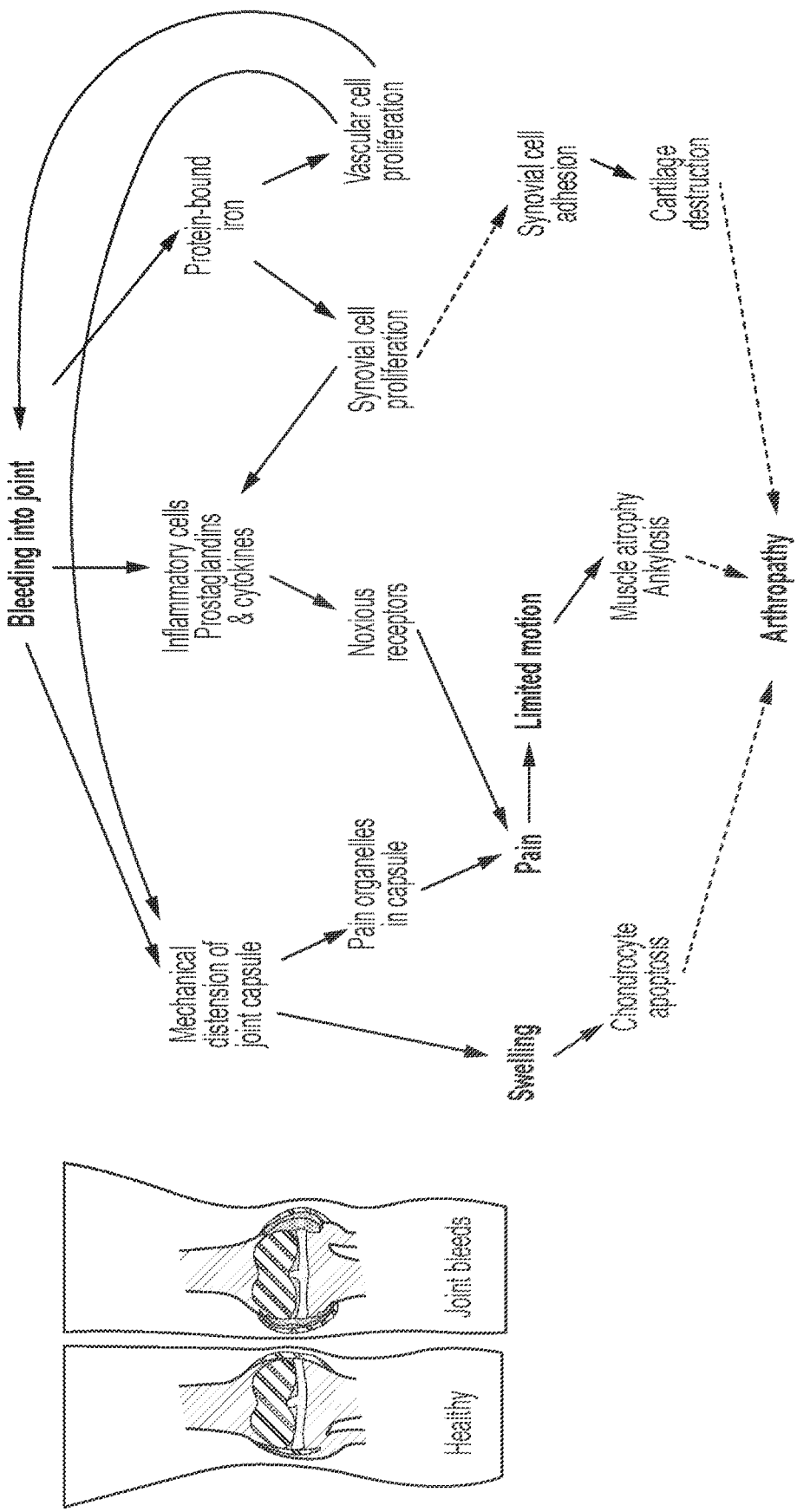
FIG. 10 is a schematic diagram of the physiopathology of hemophilic arthropathy, including a cartoon drawing of a healthy and bleeding joint.

The most common clinical manifestation of hemophilia is arthropathy secondary to recurrent hemarthroses and chronic synovitis. The knee, elbow, ankle, hip, and shoulder are the most commonly involved joints. Joint-surface erosions secondary to chronic synovitis often occur in early childhood and progress to advanced arthropathy by late adolescence (Luck Jr, J V et al. *JAAOS-J Amer Acad Orthoped Surgeons* (2004) 12(4):234-45. See FIG. 9 for a photograph. A description of the physiopathology of hemophilic arthropathy, is found, e.g., in Lafeber, F et al., (*Haemophilia,* 2008, 14 *Suppl* 4:3-9) and in FIG. 10. A mouse model of hemarthrosis is described in Example I.

A. Reduction of Swelling

Figure 11:
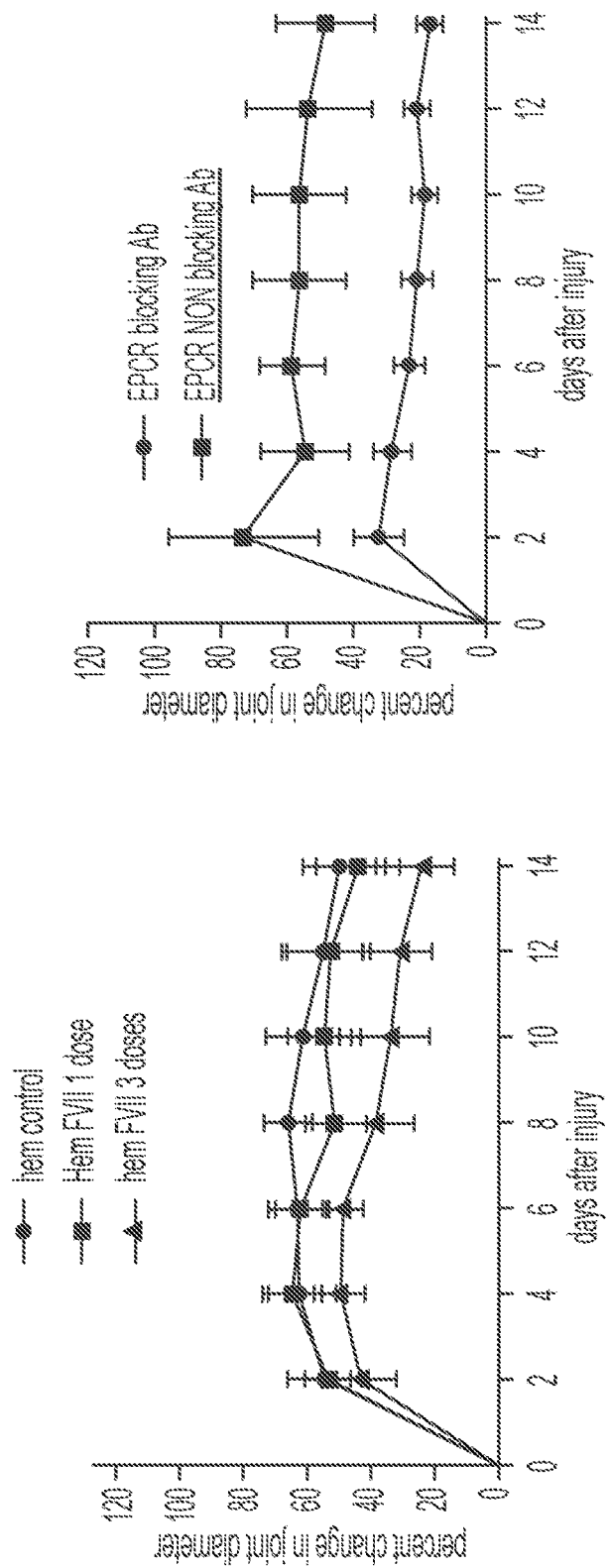
FIG. 11 shows two graphs showing the reduction in swelling (% change in joint diameter) after FVIIa (left) or EPCR antibody (right) treatment of hemophilic arthropathy. The mouse hemarthrosis model (see Example I) was used.

The results presented in FIG. 11 show reduction of swelling in joints as a result of treatment with FVIIa though more distinctly by an anti-EPCR blocking antibody.

B. Decrease in Visual Bleeding Score

Figure 12:
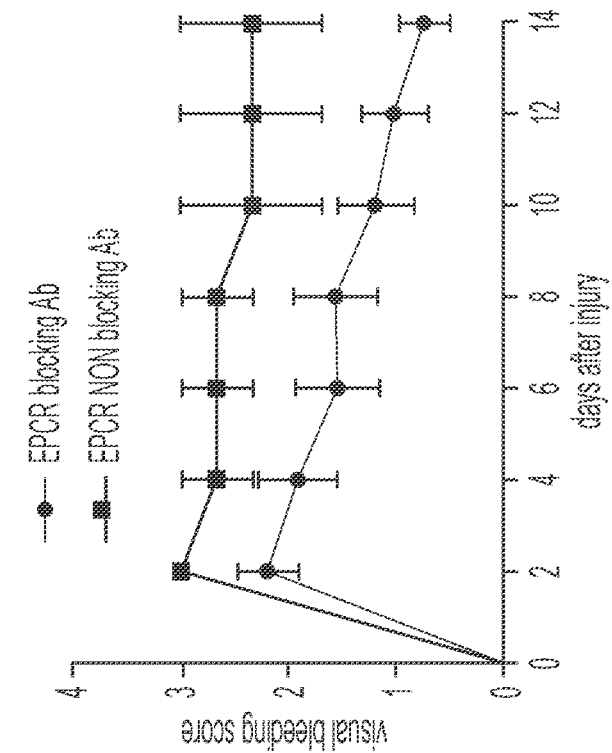
FIG. 12 shows two graphs showing the effect of FVIIa or EPCR antibody treatment in hemophilic arthropathy—measuring the amount of visual bleeding after treatment with FVIIa (left) or EPCR mAb (right). The mouse hemarthrosis model (see Example I) was used.
Figure 12:
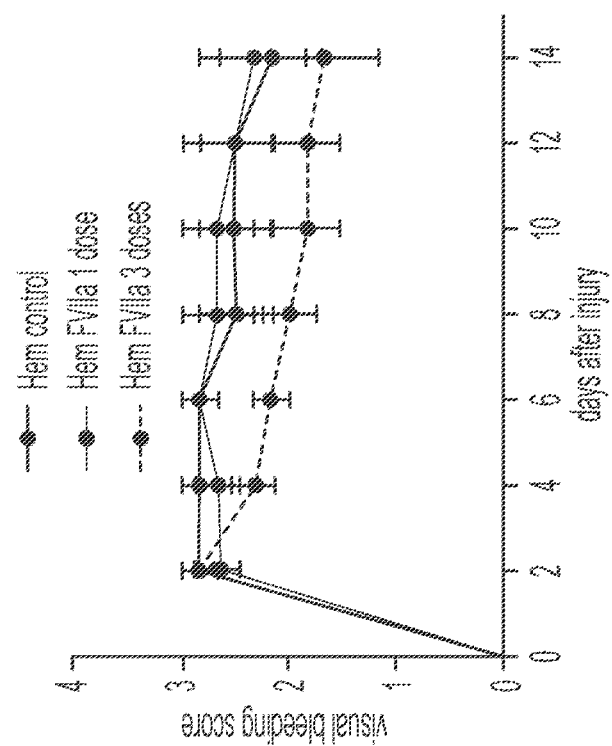

The results presented in FIG. 12 show a reduction in the visual bleeding in joints as a result of treatment with FVIIa though more distinctly by an anti-EPCR blocking antibody.

C. Inhibition of Synovitis (FIG. 13)

Figure 13:
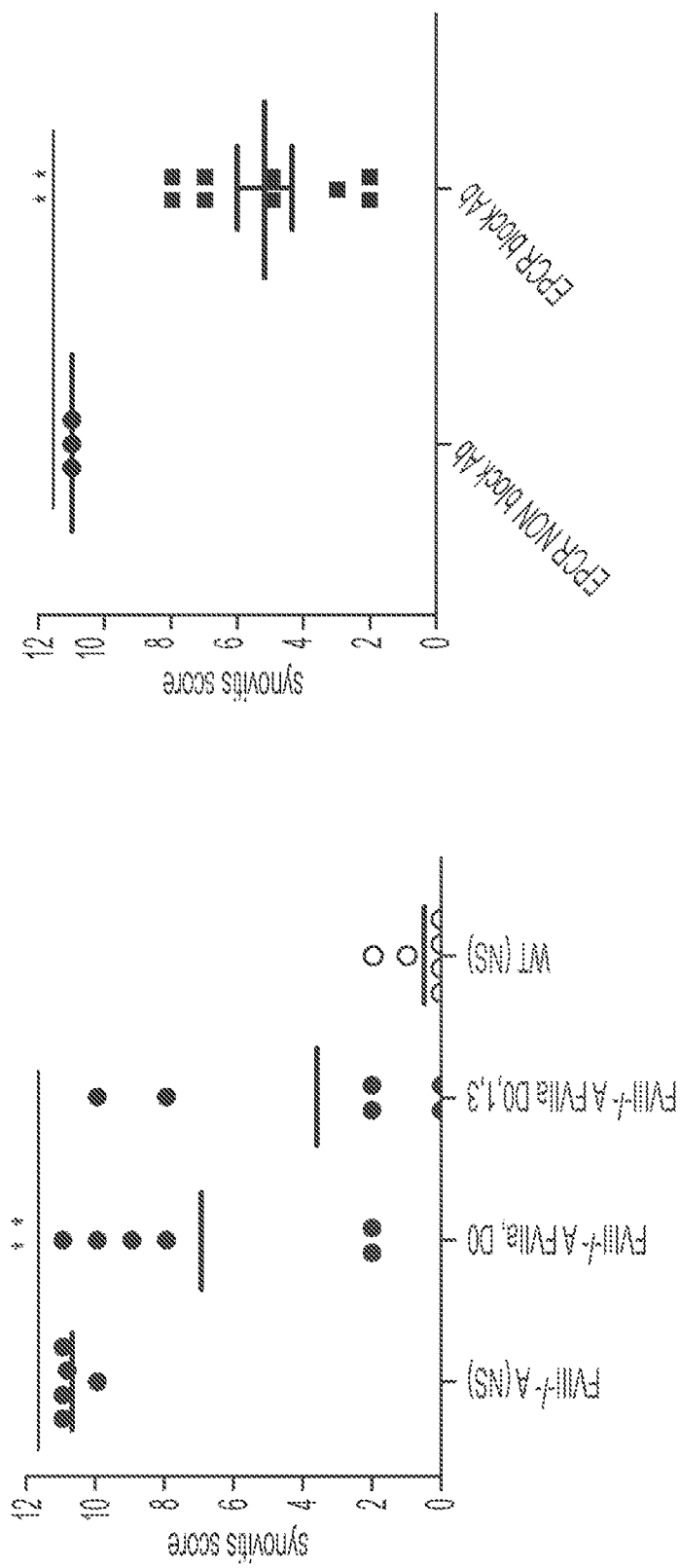
FIG. 13 shows 2 graphs showing that FVIIa (left) or blocking EPCR antibody (right) treatment reduced synovitis in a mouse hemarthrosis model (see Example I)

The results presented in FIG. 13 show a reduction in synovitis as a result of treatment with FVIIa and by anti-EPCR blocking antibody.

D. Reduction of Inflammation and Neoangiogenesis Associated with Hemophilic Arthropathy.

Figure 14:
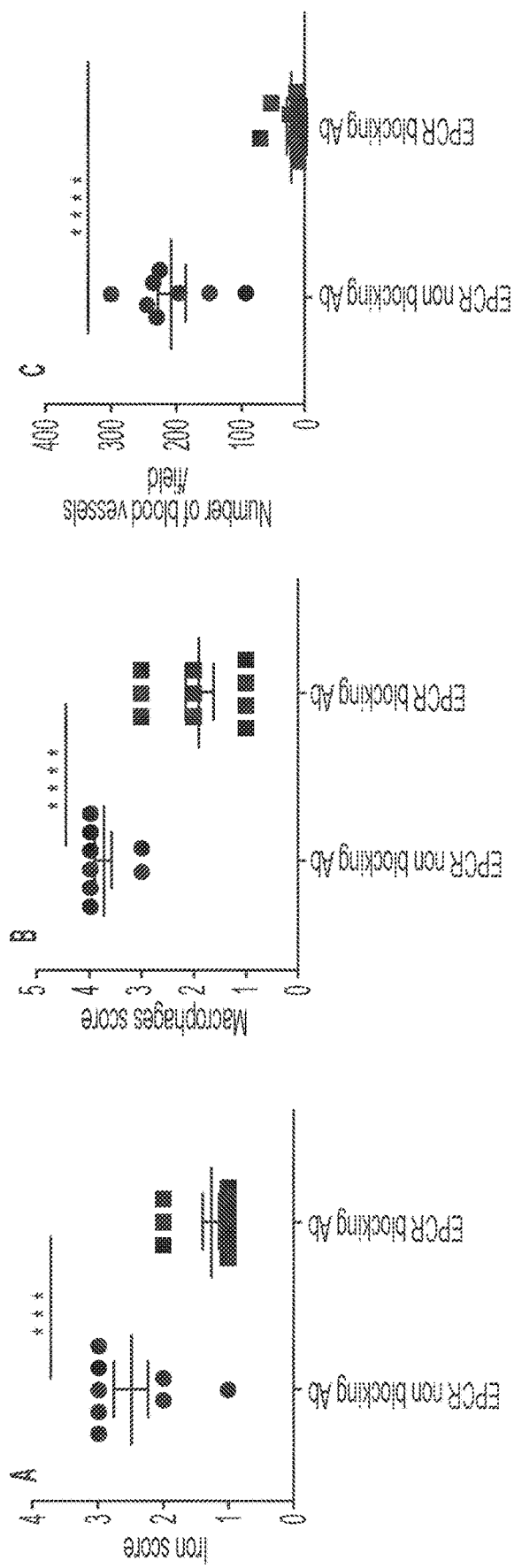
FIG. 14A-C is a series of 3 graphs showing that a single dose of EPCR blocking mAb reduces inflammation and neoangiogenesis associated with hemophilic arthropathy. Hemophilia A mice were injected with EPCR blocking or non-blocking mAb (1 mg/kg) either i.p. or i.v. Twenty four hours later, bleeding into knee joint was induced by a needle puncture injury. Fourteen days following the injury, knee joints were excised, sectioned and analyzed for iron using Prussian blue staining (FIG. 14A), macrophage infiltration using F4/80 antibody immunostaining (FIG. 14B) or neoangiogenesis by immunostaining endothelial cell marker (FIG. 14C). The intensity of iron staining was scored using 0-4 scale and the number of macrophage infiltrated scored in 0 to 4 scale. Results shown were obtained from 8 to 11 mice. *, $p<0.001$. **, $p<0.0001$.

FIG. 14A-C is a series of 3 graphs showing results of injecting Hemophilia A mice with EPCR blocking or non-blocking mAb (1 mg/kg) either i.p. or i.v. Twenty four hours later, bleeding into knee joint was induced by a needle puncture injury. Fourteen days following the injury knee joints were excised, sectioned and analyzed for iron using Prussian blue staining (FIG. 14A), macrophage infiltration using F4/80 antibody immunostaining (FIG. 14B) or neoangiogenesis by immunostaining endothelial cell marker (FIG. 14C). The results indicate that a single dose of EPCR blocking mAb reduces inflammation and neoangiogenesis associated with hemophilic arthropathy.

Figure 15:
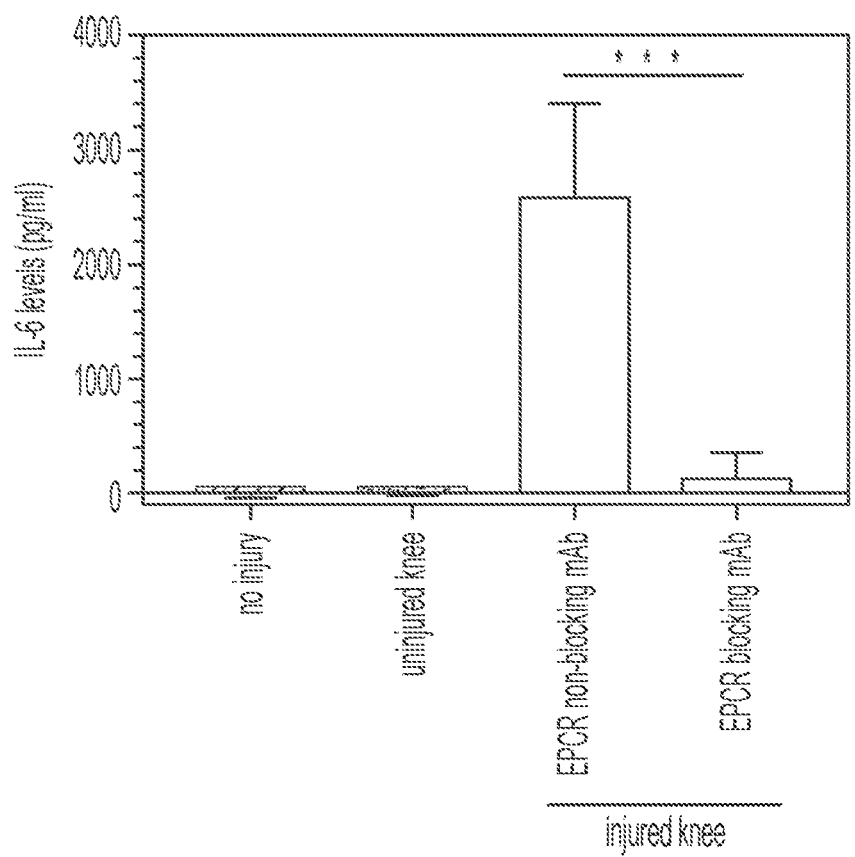
FIG. 15 is graph showing that EPCR blocking mAb prevents elaboration of the inflammatory cytokine IL-6 in the synovium associated with hemophilic arthropathy. Hemophilia A mice were injected with EPCR blocking or non-blocking mAb (1 mg/kg) either i.p. or i.v. 24 hours later, bleeding into knee joint was induced by a needle puncture injury. Seven days later, the synovial fluid from knee joints was collected and IL-6 levels in the synovial fluid was determined using IL-6 specific ELISA (n=5 to 8 mice). ***, $p<0.001$.

FIG. 15 shows results of injecting Hemophilia A mice with EPCR blocking or non-blocking mAb (1 mg/kg) either i.p. or i.v. 24 hours later, bleeding into knee joint was induced by a needle puncture injury. Seven days later, the synovial fluid from knee joints was collected and IL-6 levels in the synovial fluid were determined using IL-6 specific ELISA (n=5 to 8 mice). ***, $p<0.001$. EPCR blocking mAb also prevented elaboration of the inflammatory cytokine IL-6 in the synovium associated with hemophilic arthropathy.

E. Histopathological Studies of Arthropathy Hemophilia A joints.

A series of micrographs (FIG. 16) show representative histopathology of hemophilic arthropathy induced by needle puncture of a knee in hemophilia A mice and the effect of EPCR blocking mAb treatment. Hemophilia A mice were administered a control vehicle, EPCR non-blocking, or EPCR blocking (1 mg/kg) mAb. After 24 h, the right knee was injured by a needle puncture to induce bleeding into the knee joint. 14 days after the injury, knee joints were excised, and joint tissue sections were processed and stained with hematoxylin/eosin (H&E). Staining of joint tissue sections of uninjured left knee (no injury) was shown for comparative purposes. Arrows point out synovial thickening and synovial villi.

Figure 16:
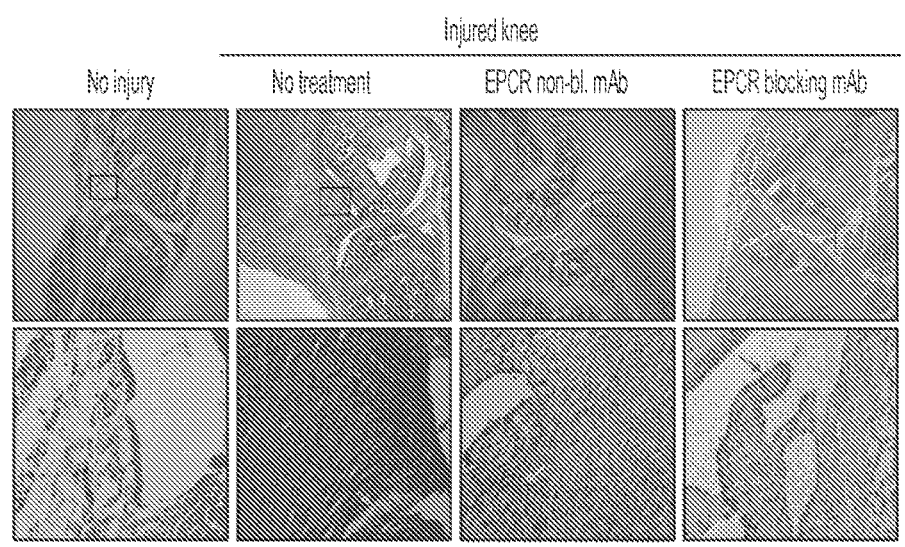
FIG. 16 is a series of 8 micrographs showing representative histopathology of hemophilic arthropathy induced by needle puncture of a knee in hemophilia A mice and effect of EPCR blocking mAb treatment. Hemophilia A mice were administered a control vehicle, EPCR non-blocking, or EPCR blocking (1 mg/kg) mAb. After 24 h, the right knee was injured by a needle puncture to induce bleeding into the knee joint. Fourteen days after the injury, knee joints were excised, and joint tissue sections were processed for hematoxylin/eosin (H&E) staining. Staining of joint tissue sections of uninjured left knee (no injury) was shown for comparative purposes. Top panel images were taken at low magnification (4×). Bottom panel images show higher magnification (40×) of areas specified in the square boxes in the top panel. Arrows point out synovial thickening and synovial villi. Images shown were representative images from 6 mice per group.
Figure 17:
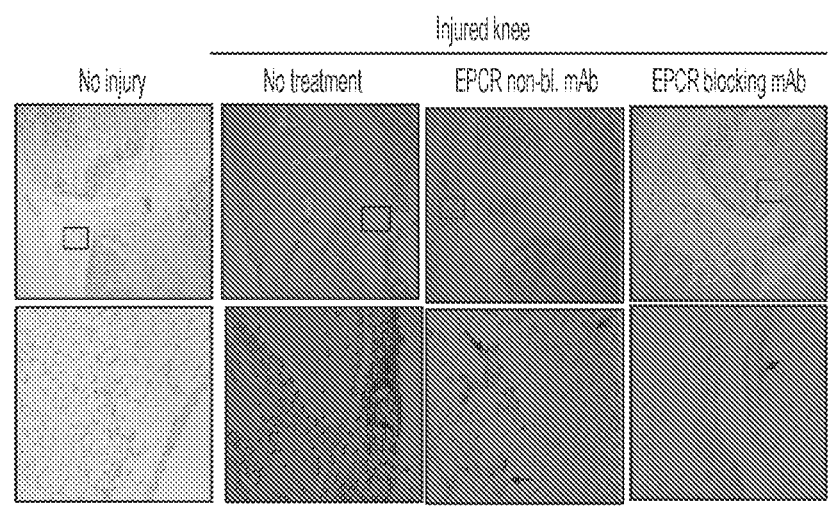
FIG. 17 is a series of 8 micrographs as in FIG. 16. Hemophilia A mice were administered a control vehicle, EPCR non-blocking, or EPCR blocking (1 mg/kg) mAb. After 24 h, the right knee was injured by a needle puncture to induce bleeding into the knee joint. 14 days after the injury, knee joints were excised, and joint tissue sections were processed for staining of free iron using Prussian blue. Iron deposits in the synovium represent free iron released from hemoglobin as a result of bleeding and destruction of red blood cells. Staining of joint tissue sections of uninjured left knee (no injury) was shown for comparative purposes. Top panel images were taken at low magnification (4×). Bottom panel images show higher magnification (40×) of areas specified in the square boxes of the top panel. Arrows point out the Prussian Blue-stained iron deposits (which are blue in a color version of the images).

A series of micrographs are presented in FIG. 17, "parallel" to those in FIG. 16. Hemophilia A mice were administered a control vehicle, EPCR non-blocking, or EPCR blocking (1 mg/kg) mAb. After 24 h, the right knee was injured by a needle puncture to induce bleeding into the knee joint. 14 days after the injury, knee joints were excised, and joint tissue sections were processed for staining of free iron using Prussian blue stain. Iron deposits in the synovium represent free iron released from hemoglobin as a results of bleeding and destruction of red blood. Staining of joint tissue sections of uninjured left knee (no injury) was shown for comparative purposes. Arrows point out the Prussian Blue-stained iron deposits. These results indicate a powerful inhibition of iron deposition in knee joints by EPCR blocking antibody in hemophilic arthropathy.

Figure 18:
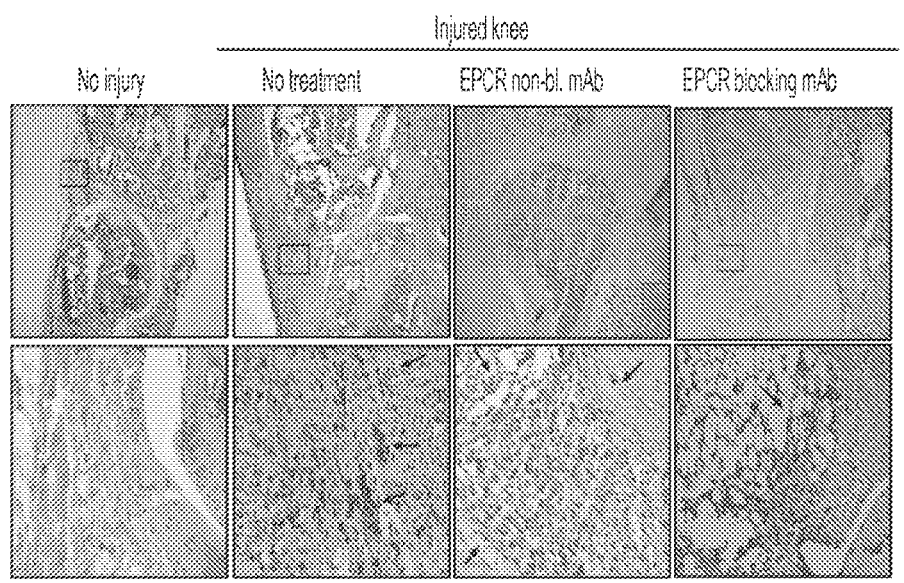
FIG. 18 is a series of 8 micrographs as in FIG. 16 showing that EPCR blocking antibody treatment reduces macrophage infiltration into the synovium associated with hemophilic arthropathy. Hemophilia A mice were administered with a control vehicle, EPCR non-blocking, or EPCR blocking (1 mg/kg) mAb. After 24 h, the right knee was injured by a needle puncture to induce bleeding into the knee joint. Fourteen days after the injury, the knee joints were excised, and joint tissue sections were processed for immunostaining with F4/80, a macrophage marker. Staining of joint tissue sections of uninjured left knee (no injury) was shown for comparative purposes. Top panel images were taken at low magnification (4×). Bottom panel images show higher magnification (40×) of areas specified in the square boxes shown in the top panel. Arrows point out stained macrophages (which are red in a color version of the images)

A series of micrographs are presented in FIG. 18, "parallel" to those in FIG. 16 Hemophilia A mice were administered with a control vehicle, EPCR non-blocking, or EPCR blocking (1 mg/kg) mAb. After 24 h, the right knee was injured by a needle puncture to induce bleeding into the knee joint. Fourteen days after the injury, the knee joints were excised, and joint tissue sections were processed for immunostaining with F4/80, a macrophage marker. Staining of joint tissue sections of uninjured left knee (no injury) was shown for comparative purposes. Arrows point out stained macrophages (which are red in a color version of the images). These results indicate that the blocking antibody treatment markedly reduces macrophage infiltration into the synovium that is associated with hemophilic arthropathy.

Figure 19:
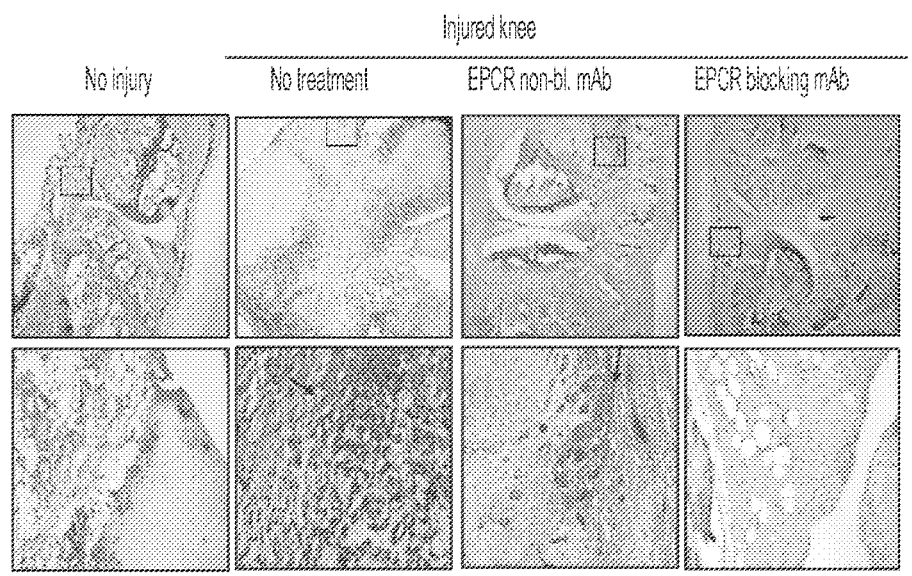
FIG. 19 is a series of 8 micrographs as in FIG. 16 showing that EPCR blocking treatment attenuates neoangiogenesis associated with hemophilic arthropathy. Hemophilia A mice were administered with control vehicle, EPCR non-blocking, or EPCR blocking (1 mg/kg) mAb. After 24 h, the right knee was injured by a needle puncture to induce bleeding into the knee joint. 14 days after the injury, the knee joints were excised, and joint tissue sections were processed for immunostaining with von Willebrand Factor (vwf) to stain endothelial cells (blood vessels). Staining of joint tissue sections of uninjured left knee (no injury) was shown for comparative purposes. Top panel images were taken at low magnification (4×). Bottom panel images show higher magnification (40×) of areas specified in the square boxes shown in the top panel. Arrows point out blood vessels.
Figure 20:
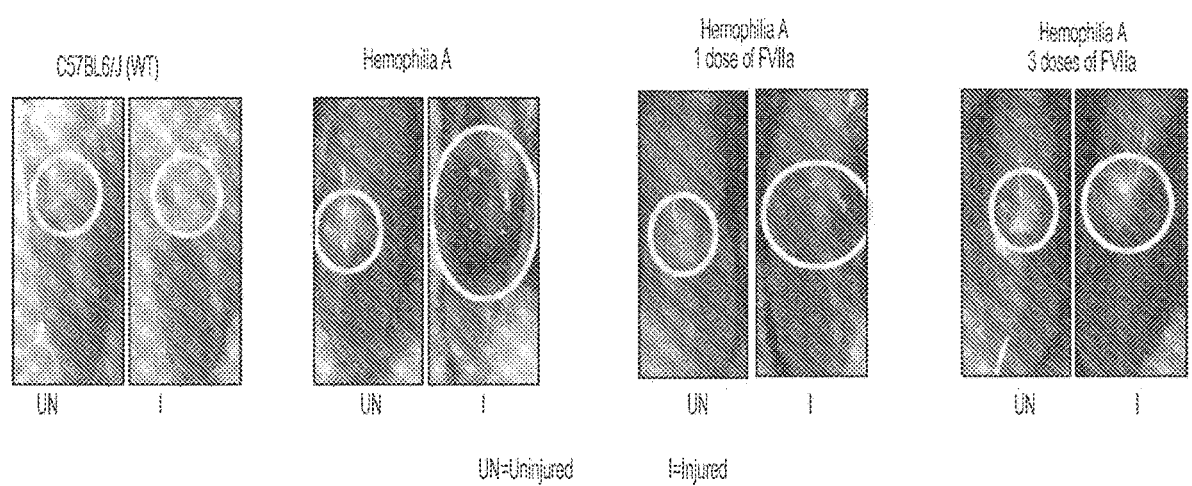
FIG. 20 is a series of (8) photographs showing that hFVIIa treatment prevents or reduces joint bleeding of hemophilic arthropathy. Knee joints of injured or uninjured mice treated with FVIIa are shown. The mouse hemarthrosis model (see Example I) was used.

A series of micrographs are presented in FIG. 19, "parallel" to those in FIG. 16 Hemophilia A mice were administered with control vehicle, EPCR non-blocking, or EPCR blocking (1 mg/kg) mAb. After 24 h, the right knee was injured by a needle puncture to induce bleeding into the knee joint. 14 days after the injury, the knee joints were excised, and joint tissue sections were processed for immunostaining with von Willebrand Factor (vwf) to stain endothelial cells (blood vessels). Staining of joint tissue sections of uninjured left knee (no injury) was shown for comparative purposes. Arrows point out blood vessels. These results indicated the blocking antibody treatment markedly attenuates neoangiogenesis that s associated with hemophilic arthropathy F. Reduction of Gross Arthropathy in Hemophilia A joints The results presented in FIG. 20 show a mild reduction in the gross appearance of arthropathy as a result of treatment with FVIIa.

Figure 21:
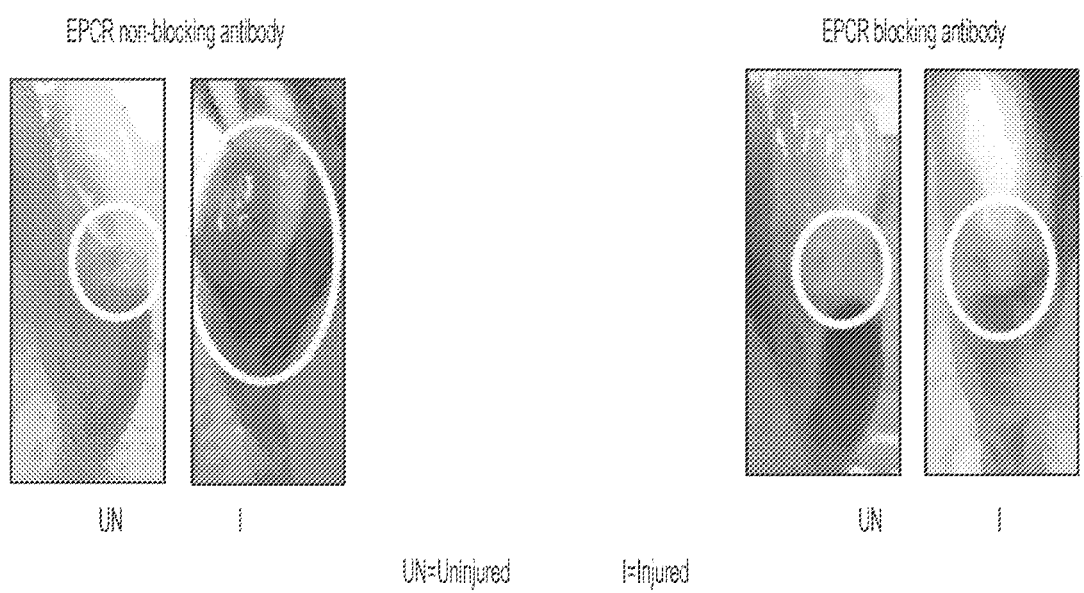
FIG. 21 is a series of (4) photographs showing that administration of EPCR blocking antibody prevents or reduces hemophilic arthropathy in a mouse model of hemarthrosis (see Example I).

The results presented in FIG. 21 show a marked reduction in the gross appearance of arthropathy as a result of treatment with a blocking EPCR Ab (vs. a non-blocking EPCR Ab

OVERALL CONCLUSIONS

The results presented herein show that EPCR antibody treatment is as effective or better than FVIIa in treating/preventing arthropathy in hemophilia, including significant reduction or attenuation in joint swelling, macrophage infiltration, iron deposition and blood vessel formation (neoangiogenesis) in the joint. As noted, the advantages of antibody treatment over that with FVIIa or other clotting proteases include:

- It is less expensive to generate/produce a mAb compared to FVIIa;
- Abs have prolonged half-life (3 to 7 days) compared to 3 hr for FVIIa;
- Abs can be administered subcutaneously (SC) whereas FVIIa must be injected into patients intravenously (IV);
- FVIIa treatment is limited to hemophilia patients with inhibitors, whereas the EPCR therapeutic is expected to be effective in all categories of hemophilia patients.

This document incorporates by reference in its entirety U.S. provisional application 62/727,613, filed Sep. 6, 2018. The references cited above are all incorporated by reference in their entirety herein, whether specifically incorporated or not. Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A method of treating a mammalian subject having hemophilic arthropathy comprising administering to said subject an effective amount of an antibody specific for Endothelial Protein C Receptor (EPCR), wherein the antibody is administered subcutaneously, and wherein the antibody is administered at a dose of 0.1 to 1 mg/kg/body weight.

2. The method of claim 1 wherein the antibody is monoclonal antibody (mAb).

3. The method of claim 2 wherein the mAb is JRK 1494.

4. The method of claim 2 wherein the mAb is JRK 1535.

5. The method of claim 1, wherein the antibody is in the form of a pharmaceutical composition that further comprises a pharmaceutically acceptable vehicle or excipient.

6. The method of claim 5, wherein factor VIIa is not administered to the mammalian subject.

7. The method of claim 1, which further comprises administration to the subject of an effective amount of recombinant factor VIIa (rVIIa).

8. The method of claim 7, wherein the method further comprises co-administration to the subject of an effective amount of active rVIIa and inactive rVIIa.

9. The method of claim 7 wherein the rVIIa is comprised in an excipient or vehicle suitable for intravenous (IV) administration.

10. The method of claim 7 wherein the rVIIa is administered IV.

11. A method of reducing or attenuating joint swelling, macrophage infiltration, iron deposition or blood vessel formation in a joint of a mammalian hemophilic subject, comprising administering to said subject an antibody specific for EPCR, and wherein the antibody is administered at a dose of 0.1 to 1 mg/kg/body weight.

12. The method of claim 11, comprising administering the antibody specific for EPCR subcutaneously.

13. The method of claim 11, further comprising co-administering an effective amount of active recombinant factor VIIa (rVIIa) and inactive rVIIa to the subject.

14. The method of claim 1, wherein the subject is a human.

15. The method of claim 5 wherein the subject is a human.

16. The method of claim 7 wherein the subject is a human.

17. The method of claim 9 wherein the subject is a human.

18. The method of claim 10 wherein the subject is a human.

19. The method of claim 11 wherein the subject is a human.

* * * * *